(12) United States Patent
Tanaka et al.

(10) Patent No.: US 11,406,086 B2
(45) Date of Patent: Aug. 9, 2022

(54) DEVICE, METHOD, AND PROGRAM FOR DETECTING INJURY OF QUADRUPED

(71) Applicant: FUJITSU LIMITED, Kawasaki (JP)

(72) Inventors: Risa Tanaka, Osaka (JP); Kiyoko Yamamoto, Kobe (JP); Osamu Shimada, Osaka (JP)

(73) Assignee: FUJITSU LIMITED, Kawasaki (JP)

( * ) Notice: Subject to any disclaimer, the term of this patent is extended or adjusted under 35 U.S.C. 154(b) by 446 days.

(21) Appl. No.: 16/054,496

(22) Filed: Aug. 3, 2018

(65) Prior Publication Data
US 2019/0045750 A1    Feb. 14, 2019

(30) Foreign Application Priority Data
Aug. 8, 2017  (JP) .............................. JP2017-153688

(51) Int. Cl.
| | | |
|---|---|---|
| *A01K 29/00* | (2006.01) | |
| *A61B 5/11* | (2006.01) | |
| *A61B 5/00* | (2006.01) | |
| *A01K 15/02* | (2006.01) | |

(52) U.S. Cl.
CPC .......... *A01K 29/005* (2013.01); *A01K 15/027* (2013.01); *A61B 5/112* (2013.01); *A61B 5/7264* (2013.01); *A61B 2503/40* (2013.01); *A61B 2562/0219* (2013.01)

(58) Field of Classification Search
None
See application file for complete search history.

(56) References Cited

U.S. PATENT DOCUMENTS

| | | | | | |
|---|---|---|---|---|---|
| 4,233,845 | A | * | 11/1980 | Pratt, Jr. .............. | A01K 29/005 73/865.4 |
| 4,935,887 | A | * | 6/1990 | Abdalah ................ | A63B 24/00 703/6 |
| 5,097,706 | A | * | 3/1992 | Le Nouvel ............ | A01K 15/02 73/493 |
| 5,736,656 | A | * | 4/1998 | Fullen ................. | A61B 5/1036 73/172 |

(Continued)

FOREIGN PATENT DOCUMENTS

| | | |
|---|---|---|
| EP | 3275369 A1 | 1/2018 |
| JP | 2008-500046 | 1/2008 |
| JP | 2016-096758 | 5/2016 |

OTHER PUBLICATIONS

EESR—Extended European search report of European Patent Application No. 18186813.4 dated Dec. 10, 2018.

(Continued)

*Primary Examiner* — Benjamin S Melhus
(74) *Attorney, Agent, or Firm* — Fujitsu Patent Center

(57) ABSTRACT

A method for detecting an injury of a quadruped includes: receiving measured data that is based on a gait of the quadruped and includes acceleration in a top-bottom direction and acceleration in a front-back direction; determining timings of putting legs of the quadruped on the ground based on the acceleration in the top-bottom direction, included in the received measured data, and determining whether or not each of the legs is injured based on values, corresponding to the determined timing of putting the legs on the ground, of the acceleration in the front-back direction.

7 Claims, 15 Drawing Sheets

(56) References Cited

U.S. PATENT DOCUMENTS

| | | | |
|---|---|---|---|
| 6,301,964 B1* | 10/2001 | Fyfe | A63B 69/0028 |
| | | | 702/160 |
| 8,398,560 B2* | 3/2013 | Elser | A61B 7/003 |
| | | | 600/534 |
| 10,149,617 B2* | 12/2018 | Couse | A61B 5/7285 |
| 10,561,365 B2* | 2/2020 | Newman | A61B 5/4812 |
| 10,610,131 B1* | 4/2020 | Thompson | A61B 5/6828 |
| 2006/0000420 A1 | 1/2006 | Martin Davies | |
| 2007/0130893 A1 | 6/2007 | Davies | |
| 2007/0208544 A1* | 9/2007 | Kulach | A61B 5/1123 |
| | | | 702/189 |
| 2008/0021352 A1* | 1/2008 | Keegan | A61B 5/1038 |
| | | | 600/595 |
| 2010/0269582 A1* | 10/2010 | Bareket | A61B 5/1124 |
| | | | 73/172 |
| 2015/0157435 A1* | 6/2015 | Chasins | A61D 13/00 |
| | | | 600/549 |
| 2016/0000373 A1* | 1/2016 | Karavirta | G01P 15/00 |
| | | | 702/19 |
| 2016/0030804 A1* | 2/2016 | Mizuochi | A61B 5/11 |
| | | | 482/8 |
| 2016/0073614 A1* | 3/2016 | Lampe | A61B 5/1128 |
| | | | 600/408 |
| 2016/0135716 A1 | 5/2016 | Yamamoto et al. | |
| 2016/0192866 A1* | 7/2016 | Norstrom | A61B 5/1123 |
| | | | 434/247 |
| 2017/0188894 A1 | 7/2017 | Chang et al. | |
| 2017/0262599 A1* | 9/2017 | Grisel | A61B 5/112 |

OTHER PUBLICATIONS

Yamamoto et al., "The Gait Analysis of Horse Riding Using Smartphone", The Japan Society of Equine Science, The Collection of the 27th Scientific Meeting Lecture Summaries, No. 18, Dec. 1, 2014. Cited in JPOA dated May 11, 2021 for Japanese Patent Application No. 2017-153688.

Fujitsu Kansai-Chubu Net-Tech Limited, "Announced Our Technology at The Collection of the 27th Scientific Meeting Lecture Summaries", Press Release, Dec. 9, 2014. Cited in JPOA dated May 11, 2021 for Japanese Patent Application No. 2017-153688.

Yamamoto et al., "The Gait Analysis of Light Horse Using Smartphone", The Japan Society of Equine Science, The Collection of the 29th Scientific Meeting Lecture Summaries, No. 34, Nov. 28, 2016. Cited in JPOA dated May 11, 2021 for Japanese Patent Application No. 2017-153688.

Fujitsu Kansai-Chubu Net-Tech Limited, "Announced Our Technology at The Collection of the 29th Scientific Meeting Lecture Summaries", Press Release, Dec. 7, 2016. Cited in JPOA dated May 11, 2021 for Japanese Patent Application No. 2017-153688.

JPOA—Japanese Office Action dated May 11, 2021 for Japanese Patent Application No. 2017-153688 with Machine Translation.

* cited by examiner

|  | A FOR LEFT LEGS | B FOR LEFT LEGS | C FOR LEFT LEGS | C FOR RIGHT LEGS | B FOR RIGHT LEGS | A FOR RIGHT LEGS |
|---|---|---|---|---|---|---|
| RIGHT FRONT LEG | 0 | 0 | 0 | 18 | 3056 | 0 |
| LEFT FRONT LEG | 9 | 3310 | 15 | 0 | 0 | 0 |
| LEFT BACK LEG | 1 | 3105 | 41 | 0 | 0 | 0 |
| RIGHT BACK LEG | 0 | 0 | 0 | 0 | 3082 | 16 |

|  | A FOR LEFT LEGS | B FOR LEFT LEGS | C FOR LEFT LEGS | C FOR RIGHT LEGS | B FOR RIGHT LEGS | A FOR RIGHT LEGS |
|---|---|---|---|---|---|---|
| RIGHT FRONT LEG | 0.00% | 0.00% | 0.00% | 0.59% | 99.41% | 0.00% |
| LEFT FRONT LEG | 0.27% | 99.28% | 0.45% | 0.00% | 0.00% | 0.00% |
| LEFT BACK LEG | 0.03% | 98.67% | 1.30% | 0.00% | 0.00% | 0.00% |
| RIGHT BACK LEG | 0.00% | 0.00% | 0.00% | 0.00% | 99.48% | 0.52% |

AREAS ASSOCIATED WITH TIMING OF PUTTING LEGS ON GROUND ARE CLASSIFIED INTO THREE GROUPS A, B, AND C

⬇

⬇

NUMBERS BELONGING TO GROUPS ARE CALCULATED

⬇

| | A FOR LEFT LEGS | B FOR LEFT LEGS | C FOR LEFT LEGS | C FOR RIGHT LEGS | B FOR RIGHT LEGS | A FOR RIGHT LEGS | |
|---|---|---|---|---|---|---|---|
| RIGHT FRONT LEG | 0 | 0 | 0 | 18 | 3056 | 0 | 37a |
| LEFT FRONT LEG | 9 | 3310 | 15 | 0 | 0 | 0 | 37c |
| LEFT BACK LEG | 1 | 3105 | 41 | 0 | 0 | 0 | |
| RIGHT BACK LEG | 0 | 0 | 0 | 0 | 3082 | 16 | 39a |

| LAME LEG | RIGHT FRONT LEG | RIGHT BACK LEG | LEFT FRONT LEG | LEFT BACK LEG |
|---|---|---|---|---|
| LEGS AFFECTED AND LEG UNAFFECTED UPON PUTTING OF LAME LEG ON GROUND | | | | |
| RIGHT FRONT LEG | INJURED | AFFECTED | AFFECTED | UNAFFECTED |
| RIGHT BACK LEG | UNAFFECTED | INJURED | AFFECTED | AFFECTED |
| LEFT FRONT LEG | AFFECTED | UNAFFECTED | INJURED | AFFECTED |
| LEFT BACK LEG | AFFECTED | AFFECTED | UNAFFECTED | INJURED |
| CHANGES IN BEHAVIORS OF LAME LEG AND OTHER LEGS UPON PUTTING OF LEGS ON GROUND | | | | |
| UPON PUTTING OF RIGHT FRONT LEG ON GROUND | LAME LEG =BACKWARD ACCELERATION THAT NORMALLY OCCURS IS REDUCED | LEG THAT IS PUT ON GROUND AFTER LAME LEG =FRONTWARD ACCELERATION OCCURS SINCE HORSE QUICKLY PUTS LEG ON GROUND TO PROTECT LAME LEG | NORMAL BACKWARD ACCELERATION OCCURS | NORMAL BACKWARD ACCELERATION OCCURS |
| UPON PUTTING OF RIGHT BACK LEG ON GROUND | NORMAL FRONTWARD ACCELERATION OCCURS | LAME LEG =FRONTWARD ACCELERATION THAT NORMALLY OCCURS IS REDUCED | LEG THAT IS PUT ON GROUND AFTER LAME LEG =FRONTWARD ACCELERATION THAT NORMALLY OCCURS IS REDUCED SINCE HORSE QUICKLY PUTS LEG ON GROUND TO PROTECT LAME LEG | NORMAL FRONTWARD ACCELERATION OCCURS |
| UPON PUTTING OF LEFT FRONT LEG ON GROUND | NORMAL BACKWARD ACCELERATION OCCURS | NORMAL BACKWARD ACCELERATION OCCURS | LAME LEG =BACKWARD ACCELERATION THAT NORMALLY OCCURS IS REDUCED | LEG THAT IS PUT ON GROUND AFTER LAME LEG =FRONTWARD ACCELERATION OCCURS SINCE HORSE QUICKLY PUTS LEG ON GROUND TO PROTECT LAME LEG |
| UPON PUTTING OF LEFT BACK LEG ON GROUND | LEG THAT IS PUT ON GROUND AFTER LAME LEG =FRONTWARD ACCELERATION THAT NORMALLY OCCURS IS REDUCED SINCE HORSE QUICKLY PUTS LEG ON GROUND TO PROTECT LAME LEG | NORMAL FRONTWARD ACCELERATION OCCURS | NORMAL FRONTWARD ACCELERATION OCCURS | LAME LEG =FRONTWARD ACCELERATION THAT NORMALLY OCCURS IS REDUCED |

DEVICE, METHOD, AND PROGRAM FOR DETECTING INJURY OF QUADRUPED

CROSS-REFERENCE TO RELATED APPLICATION

This application is based upon and claims the benefit of priority of the prior Japanese Patent Application No. 2017-153688, filed on Aug. 8, 2017, the entire contents of which are incorporated herein by reference.

FIELD

The embodiments discussed herein are related to a device for detecting an injury of a quadruped, a method for detecting an injury of a quadruped, and a program for detecting an injury of a quadruped.

BACKGROUND

For example, racehorses are trained by horse trainers who are managers to cause stress on minds and bodies of the horses in order to improve abilities of the horses. However, since horses including racehorses are living organisms, physical conditions of the horses may change day by day, and the horses may in bad conditions. One of physically bad conditions of horses is lameness that is an abnormal gait. Lameness may occur before an injury becomes major in many cases, and it is important to find lameness early in order to protect a horse. Traditionally, lameness has been found by horse managers based on their experience and instinct, but it may be hard to distinguish minor lameness and a normal state, and minor lameness may be overlooked. To avoid this, the idea of attaching various sensors to horse legs and the like and detecting lameness has been proposed. In fact, however, it is hard to attach the sensors to legs of a sensitive racehorse. In addition, the idea of attaching various sensors to a horse body and the like and detecting lameness from data measured during trotting has been proposed.

Examples of related art are Japanese National Publication of International Patent Application No. 2008-500046 and Japanese Laid-open Patent Publication No. 2016-096758.

However, when a person makes a horse trot to detect lameness, the trot causes larger stress on the horse than that caused by walking. Thus, lameness may become worse due to physical stress on the horse in some cases.

According to an aspect, an object is to provide a device for detecting an injury of a quadruped, a method for detecting an injury of a quadruped, and a program for detecting an injury of a quadruped, which may detect an injury without causing physical stress.

SUMMARY

According to an aspect of the invention, a method for detecting an injury of a quadruped includes: receiving measured data that is based on a gait of the quadruped and includes acceleration in a top-bottom direction and acceleration in a front-back direction; determining timings of putting legs of the quadruped on the ground based on the acceleration in the top-bottom direction, included in the received measured data, and determining whether or not each of the legs is injured based on values, corresponding to the determined timing of putting the legs on the ground, of the acceleration in the front-back direction.

The object and advantages of the invention will be realized and attained by means of the elements and combinations particularly pointed out in the claims.

It is to be understood that both the foregoing general description and the following detailed description are exemplary and explanatory and are not restrictive of the invention, as claimed.

BRIEF DESCRIPTION OF DRAWINGS

FIG. 6 is a diagram illustrating an example of an analyzed data storage section;

FIG. 7 is a diagram illustrating another example of the analyzed data storage section;

FIG. 13 is a diagram illustrating an example of a lame leg determination table;

DESCRIPTION OF EMBODIMENTS

Hereinafter, embodiments of a device disclosed herein for detecting an injury of a quadruped, a method disclosed herein for detecting an injury of a quadruped, and a program disclosed herein for detecting an injury of a quadruped are described below in detail based on the accompanying drawings. Techniques disclosed herein are not limited to the embodiments. In addition, the embodiments may be combined without contradiction.

EMBODIMENTS

Figure 1:
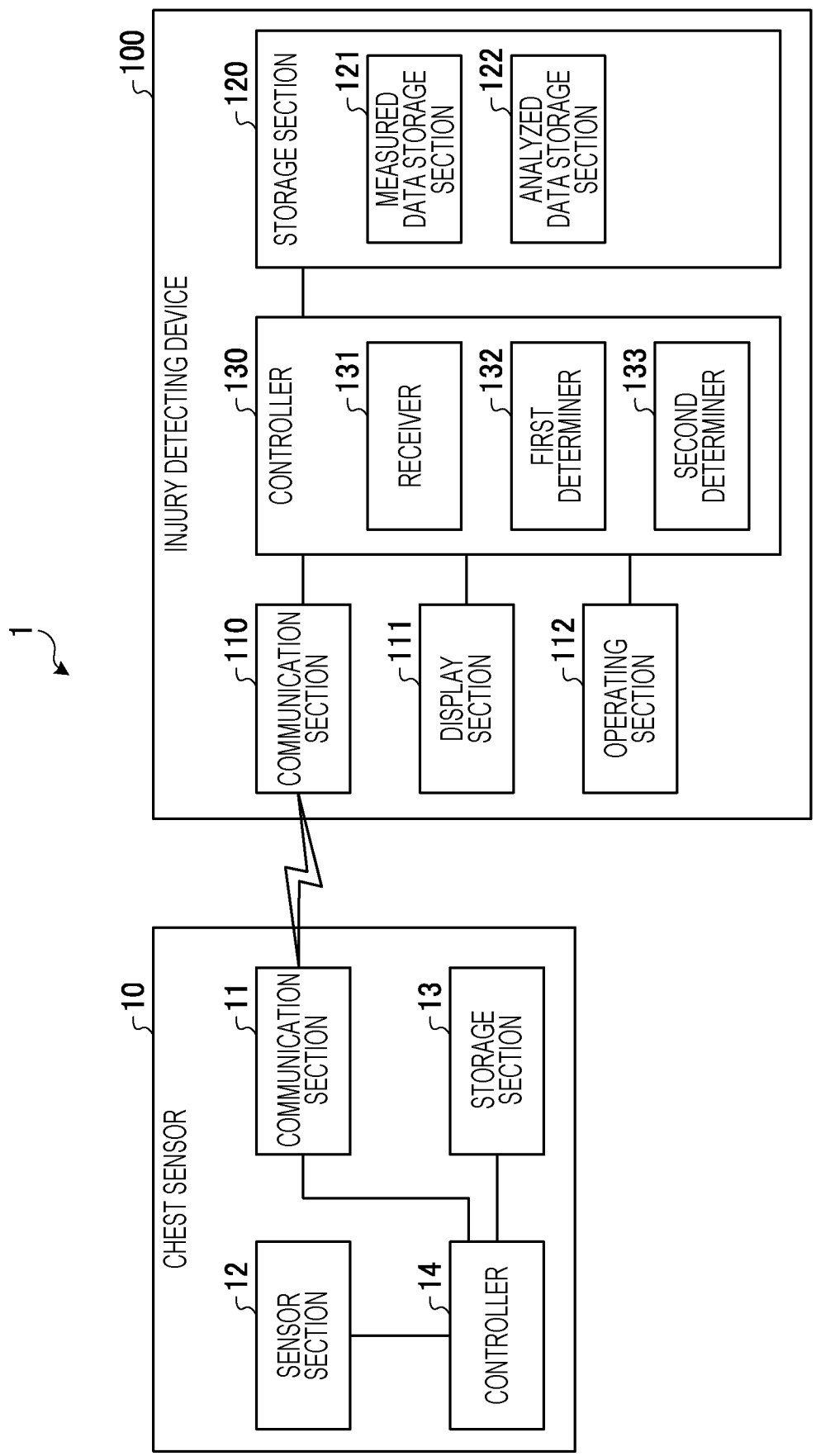
FIG. 1 is a block diagram illustrating an example of the configuration of an injury detection system according to an embodiment.

FIG. 1 is a block diagram illustrating an example of the configuration of an injury detection system according to an embodiment. An injury detection system 1 illustrated in FIG.

1 includes a chest sensor 10 and an injury detecting device 100. Although FIG. 1 illustrates the case where the injury detection system 1 includes the single chest sensor 10 and the single injury detecting device 100, the number of chest sensors 10 and the number of injury detecting devices 100 are not limited. In other words, the injury detection system 1 may include an arbitrary number of chest sensors 10 and an arbitrary number of injury detecting devices 100.

The chest sensor 10 and the injury detecting device 100 are connected to each other and able to communicate with each other via a wireless local area network (LAN) access point not illustrated, for example. The chest sensor 10 and the injury detecting device 100 may communicate directly with each other using Wi-Fi Direct (registered trademark) or the like without an access point. The chest sensor 10 and the injury detecting device 100 may be connected to each other via a cable.

The injury detection system 1 is an example of a system in which the injury detecting device 100 receives data measured by the chest sensor 10 attached to the chest of a horse and analyzes the received data. The chest sensor 10 measures acceleration in a top-bottom direction, acceleration in a left-right direction, acceleration in a front-back direction, and an angular velocity about a yaw axis based on the gait of the horse and generates the measured data. The chest sensor 10 transmits the generated measured data to the injury detecting device 100. In the following description, the acceleration in the top-bottom direction, the acceleration in the left-right direction, the acceleration in the front-back direction, and the angular velocity about the yaw axis are referred to as top-bottom acceleration, left-right acceleration, front-back acceleration, and yaw-axis angular velocity in some cases.

The injury detecting device 100 is an information processing device that is used by a stable keeper, a horse trainer who is a manager of the racehorse, or the like. The injury detecting device 100 determines, based on the measured data received from the chest sensor 10, whether or not legs of the racehorse are lame. Specifically, the injury detecting device 100 receives the measured data that is based on the gait of the quadruped and includes the acceleration in the top-bottom direction and the acceleration in the front-back direction. The injury detecting device 100 determines, based on the top-bottom acceleration included in the received measured data, the timing of putting the legs on the ground. The injury detecting device 100 determines whether or not each of the legs is injured based on values, corresponding to the determined timing of putting the legs on the ground, of the acceleration in the front-back direction. Thus, the injury detecting device 100 may detect an injury without causing physical stress.

Next, the configuration of the chest sensor 10 is described. As illustrated in FIG. 1, the chest sensor 10 includes a communication section 11, a sensor section 12, a storage section 13, and a controller 14. The chest sensor 10 may include not only the functional sections illustrated in FIG. 1 but also various functional sections such as an input device and an output device, for example.

The communication section 11 is achieved by a communication module or the like such as a wireless LAN, for example. The communication section 11 is, for example, a communication interface that is wirelessly connected to the injury detecting device 100 via a wireless LAN and communicates information with the injury detecting device 100. The communication section 11 transmits the measured data received from the controller 14 to the injury detecting device 100.

The sensor section 12 is a device that detects the top-bottom acceleration, the left-right acceleration, the front-back acceleration, and the yaw-axis angular velocity that are based on the gait of the horse. The sensor section 12 includes a triaxial acceleration sensor that serves as a device for measuring acceleration and measures acceleration in three axial directions, an X-axis direction, a Y-axis direction, and a Z-axis direction, which are perpendicular to each other, for example. Specifically, the triaxial acceleration sensor may measure the left-right acceleration, the front-back acceleration, and the top-bottom acceleration by treating the left-right direction as the X axis, the front-back direction as the Y axis, and the top-bottom direction as the Z axis, for example. In addition, the sensor section 12 includes a gyrosensor as a device for measuring angular velocities about the X, Y, and Z axes. As the acceleration sensor, a piezo-resistive triaxial accelerometer, a capacitance triaxial accelerometer, or the like may be used, for example. As the gyrosensor, a vibration gyrosensor may be used, for example. The sensor section 12 generates the measured data based on data of the measured top-bottom acceleration, data of the measured left-right acceleration, data of the measured front-back acceleration, and data of the measured yaw-axis angular velocity and outputs the generated measured data to the controller 14.

The storage section 13 is achieved by a storage device such as a semiconductor memory element or the like such as a random access memory (RAM) or a flash memory, for example. The storage section 13 stores the data measured by the sensor section 12. In addition, the storage section 13 stores information to be used for a process to be executed by the controller 14. The storage section 13 may be detachable and may be a portable recording medium such as an SD memory card, for example. In this case, the injury detecting device 100 may include a reading device for reading the data from the portable recording medium, and the measured data may be migrated to the injury detecting device 100.

The controller 14 is achieved by causing a central processing unit (CPU), a micro processing unit (MPU), or the like to use a RAM as a work region to execute a program stored in an internal storage device, for example. Alternatively, the controller 14 may be achieved by an integrated circuit such as an application specific integrated circuit (ASIC) or a field programmable gate array (FPGA), for example.

The controller 14 causes the measured data received from the sensor section 12 to be stored in the storage section 13. In addition, when the chest sensor 10 is wirelessly connected to the injury detecting device 100, the controller 14 reads the measured data stored in the storage section 13 and transmits the measured data to the injury detecting device 100 via the communication section 11. The measured data may be data measured during a time period of approximately 1 minute to 2 minutes in order to suppress an effect of looking away and a noise effect but may be data measured during a longer time period.

Figure 2:
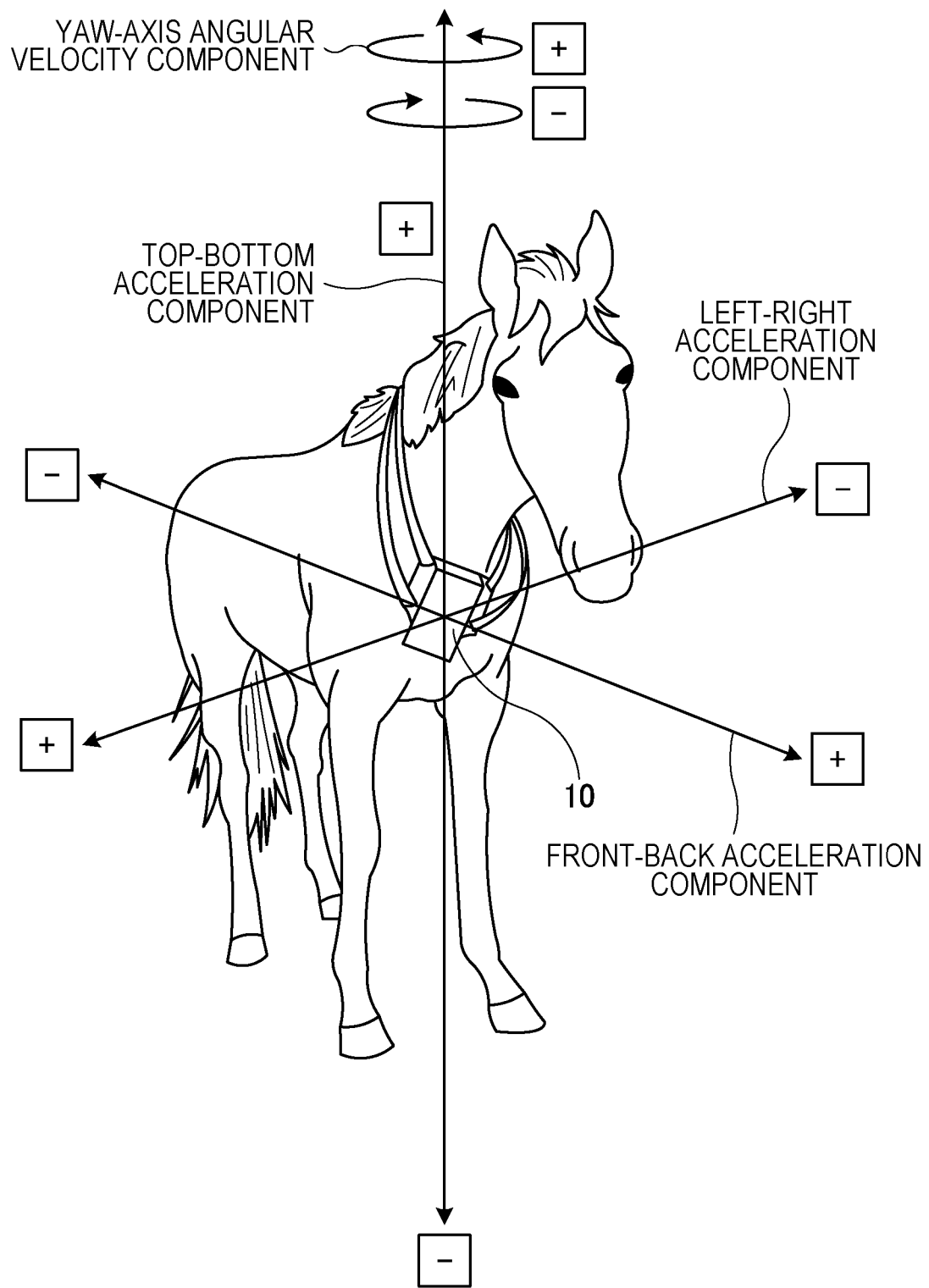
FIG. 2 is a diagram illustrating an example of a chest sensor and an example of components of measured data.

The measured data is described below with reference to FIGS. 2 to 5. FIG. 2 is a diagram illustrating an example of the chest sensor and an example of components of the measured data. As illustrated in FIG. 2, the chest sensor 10 is attached to the chest of the horse. Data measured by the chest sensor 10 includes a top-bottom acceleration component, a left-right acceleration component, and a front-back acceleration component in the three axes, the top-bottom direction of the horse, the left-right direction of the horse, and the front-back direction of the horse. In addition, the measured data includes a yaw-axis angular velocity component in a rotational direction about an axis extending in the top-bottom direction. Regarding the top-bottom acceleration component, an upward direction with respect to the horse is defined as positive in the top-bottom direction, and a downward direction with respect to the horse is defined as negative in the top-bottom direction. Regarding the left-right acceleration component, a rightward direction with respect to a movement direction of the horse is defined as positive in the left-right direction, and a leftward direction with respect to the movement direction of the horse is defined as negative in the left-right direction. Regarding the front-back acceleration component, the movement direction of the horse is defined as positive in the front-back direction, and a direction (backward direction) opposite to the movement direction of the horse is defined as negative in the front-back direction. Regarding the yaw-axis angular velocity component, a clockwise direction when viewed from the bottom of the horse toward the top of the horse in the top-bottom direction is defined as positive in the yaw axis direction, and a counterclockwise direction when viewed from the bottom of the horse toward the top of the horse in the top-bottom direction is defined as negative in the yaw axis direction.

Figure 3:
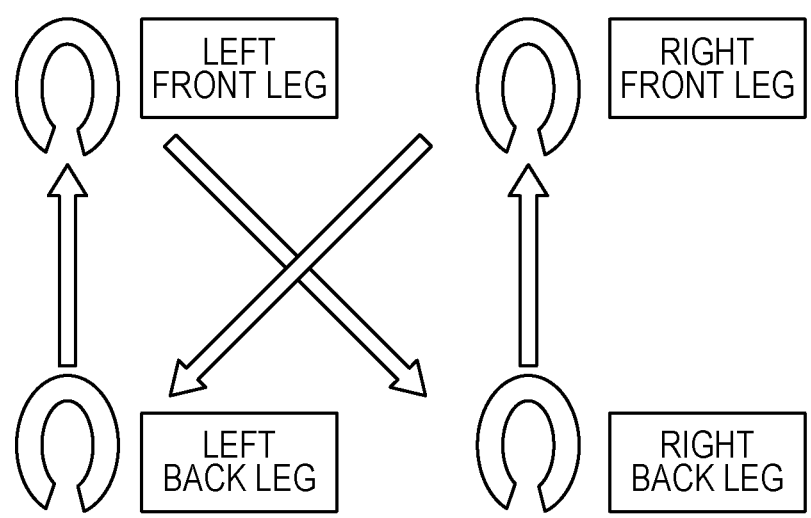
FIG. 3 is a diagram illustrating an example of the order in which a horse puts four legs on the ground during walking.

FIG. 3 is a diagram illustrating an example of the order in which the horse puts the four legs on the ground during walking. As illustrated in FIG. 3, the horse puts the right front leg, the left back leg, the left front leg, and the right back leg on the ground in this order during one stride when walking, for example. When the horse walks, the horse repeatedly puts the legs on the ground in the aforementioned order. When the horse trots, canters, or gallops, the order in which the horse puts the legs on the ground is different from the aforementioned order.

Figure 4:
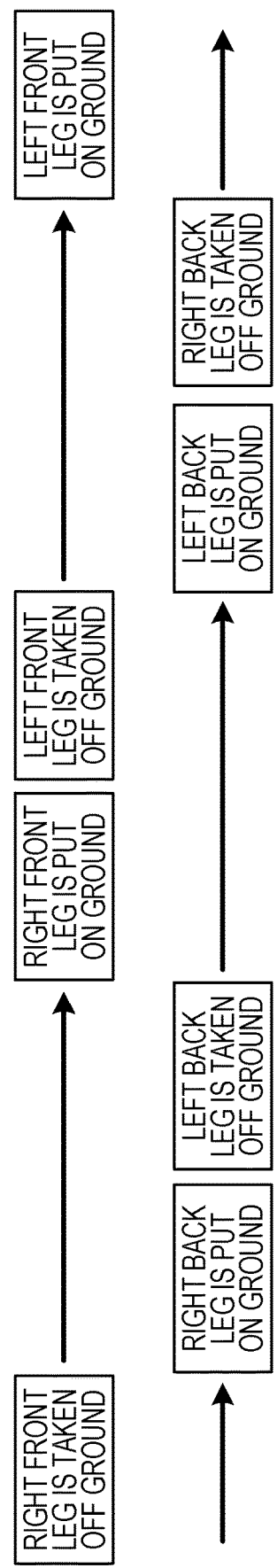
FIG. 4 is a diagram illustrating an example of the order in which the horse puts and takes the four legs on and off the ground during walking.

FIG. 4 is a diagram illustrating an example of the order in which the horse puts and takes the four legs on and off the ground during walking. As illustrated in FIG. 4, during walking, the horse takes the right front leg off the ground in a state in which the horse takes the right back leg off the ground, and the horse puts the right back leg on the ground after taking the right front leg off the ground. Next, the horse takes the left back leg off the ground, puts the right front leg on the ground, takes the left front leg off the ground, and puts the left back leg on the ground. Next, the horse takes the right back leg off the ground and puts the left front leg on the ground. During walking, the horse repeatedly puts and takes the four legs on and off the ground in this order.

Figure 5:
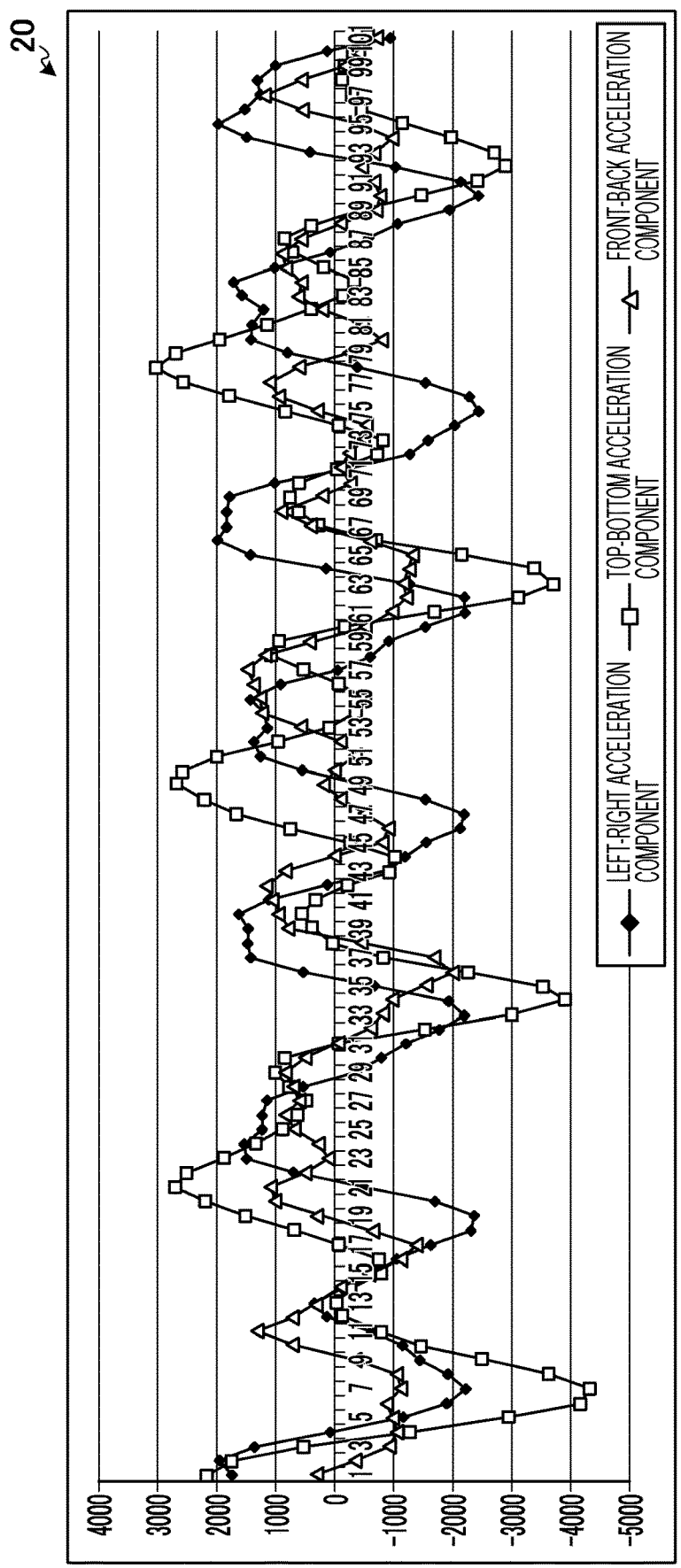
FIG. 5 is a diagram illustrating an example of data measured during walking.

FIG. 5 is a diagram illustrating an example of data measured during walking. A graph 20 illustrated in FIG. 5 is obtained by plotting a left-right acceleration component, a top-bottom acceleration component, and a front-back acceleration component that are included in the measured data. As indicated in the graph 20, it is apparent that the acceleration components periodically repeatedly change. In the example illustrated in FIG. 5, the acceleration components are data measured at time intervals of 40 milliseconds. Plotted values, amplitude, periods, waveforms, and the like of the measured data may vary depending on the horse.

Next, the configuration of the injury detecting device 100 is described. As illustrated in FIG. 1, the injury detecting device 100 includes a communication section 110, a display section 111, an operating section 112, a storage section 120, and a controller 130. The injury detecting device 100 may include not only the functional sections illustrated in FIG. 1 but also various functional functions that are included in an existing computer and are an input device, an output device, and the like, for example.

The communication section 110 is achieved by a communication module or the like such as a wireless LAN, for example. The communication section 110 is, for example, a communication interface that is wirelessly connected to the chest sensor 10 via the wireless LAN and communicates information with the chest sensor 10. The communication section 110 receives the measured data from the chest sensor 10. The communication section 110 outputs the received measured data to the controller 130.

The display section 111 is a display device that displays various types of information. The display section 111 is achieved by a liquid crystal display or the like as a display device, for example. The display section 111 displays various screens including a display screen received from the controller 130.

The operating section 112 is an input device that receives various operations from a user of the injury detecting device 100. The operating section 112 is achieved by a keyboard, a mouse, or the like as an input device, for example. The operating section 112 outputs, as operational information, an operation input by the user to the controller 130.

The storage section 120 is achieved by a storage device such as a semiconductor memory element that is a RAM, a flash memory, or the like, a hard disk, an optical disc, or the like, for example. The storage section 120 includes a measured data storage section 121 and an analyzed data storage section 122. In addition, the storage section 120 stores information to be used for a process to be executed by the controller 130.

The measured data storage section 121 stores the measured data. The measured data storage section 121 associates values of the top-bottom acceleration, the left-right acceleration, the front-back acceleration, and the yaw-axis angular velocity with data numbers and stores the values associated with the data numbers. Each of the data numbers is a uniquely assigned number and is an identifier identifying measured data. The three types of acceleration and the angular velocity are measured at the time intervals of 40 milliseconds, for example. Top-bottom acceleration, left-right acceleration, front-back acceleration, and an angular velocity that are measured at the same time are associated with the same data number.

The analyzed data storage section 122 stores analyzed data obtained by classifying the timing of putting the legs on the ground into multiple groups based on values, corresponding to the timing of putting the legs on the ground, of the front-back acceleration. FIG. 6 is a diagram illustrating an example of the analyzed data storage section. As illustrated in FIG. 6, in the analyzed data storage section 122, an abscissa indicates three groups A, B, and C for the left legs and three groups A, B, and C for the right legs. In the analyzed data storage section 122, an ordinate indicates the four legs. In the example illustrated in FIG. 6, in a first row indicating that the numbers of times that the horse puts the right front leg on the ground, the group A for the right legs indicates "0", the group B for the right legs indicates "3056", and the group C for the right legs indicates "18". In the example illustrated in FIG. 6, since the first row indicates the numbers of times that the horse puts the right front leg on the ground, the groups A, B, and C for the left legs indicate "0" in the first row.

FIG. 7 is a diagram illustrating another example of the analyzed data storage section. An analyzed data storage section 122a illustrated in FIG. 7 indicates percentages of data included in the analyzed data storage section 122 illustrated in FIG. 6. The analyzed data storage section 122 may use percentages to indicate the numbers of times that the horse puts each of the legs on the ground. In the examples illustrated in FIGS. 6 and 7, if the area of a range within a time interval between time points when the horse puts legs on the ground is associated with the earlier one of the time points when the horse puts the legs on the ground, the numbers of times that the horse puts the legs on the ground may be indicated by the numbers of time intervals at which when the horse puts the legs on the ground, for example. Details are described later with reference to FIG. 11.

Return to FIG. 1. The controller 130 is achieved by causing a CPU, an MPU, or the like to use a RAM as a work region to execute a program stored in an internal storage device, for example. Alternatively, the controller 130 may be achieved by an integrated circuit such as an ASIC or an FPGA, for example. The controller 130 includes a receiver 131, a first determiner 132, and a second determiner 133. The controller 130 executes information processing functions described later or achieves information processing effects described later. An internal configuration of the controller 130 is not limited to the configuration illustrated in FIG. 1. The controller 130 may have another configuration as long as information processing described later is executed in the configuration.

The receiver 131 receives the measured data from the chest sensor 10 via the communication section 110. The receiver 131 causes the received measured data to be stored in the measured data storage section 121. A reading device not illustrated may read the measured data from a portable recording medium storing the measured data, and the receiver 131 may receive the measured data from the reading device. After the receiver 131 causes the measured data to be stored in the measured data storage section 121, the receiver 131 outputs, to the first determiner 132, an instruction to determine the timing of putting the legs on the ground.

Specifically, the receiver 131 receives the measured data that is based on the gait of the quadruped and includes the acceleration in the top-bottom direction and the acceleration in the front-back direction. The receiver 131 receives the data measured during walking. The receiver 131 receives the measured data including the angular velocity about the yaw axis.

Upon receiving the instruction to determine the timing of putting the legs on the ground from the receiver 131, the first determiner 132 references the measured data storage section 121 and determines, based on the measured data, the timing of putting the legs on the ground and the left or right of each of the legs. First, the first determiner 132 determines, based on the top-bottom acceleration, the timing of putting the front legs on the ground. For example, the first determiner 132 determines that the time when the top-bottom acceleration is reversed from negative to positive and from positive to negative is the time when the horse puts the front legs on the ground. This is due to the fact that the chest sensor 10 attached to the chest is lifted and the top-bottom acceleration component is reversed from negative to positive or from positive to negative due to the putting of a front leg on the ground. The first determiner 132 determines that the horse puts one of the back legs on the ground at midpoints in time between the time when the horse puts one of the front legs on the ground and the time when the horse puts the other one of the front legs on the ground, and that the horse puts the other one of the back legs on the ground at midpoints in time between the time when the horse puts the other one of the front legs on the ground and the time when the horse puts the one of the front legs on the ground.

Next, the first determiner 132 determines, based on the yaw-axis angular velocity, the timing of taking the front legs off the ground and the left or right of each of the legs. For example, the first determiner 132 determines that the time when the sign of the yaw-axis angular velocity is reversed to positive is the time when the horse takes the right front leg off the ground. In addition, for example, the first determiner 132 determines that the time when the sign of the yaw-axis angular velocity is reversed to negative is the time when the horse takes the left front leg off the ground. The sign of the yaw-axis angular velocity varies depending on which rotational direction about the axis extending in the top-bottom direction is treated as positive, as illustrated in FIG. 2.

Next, the first determiner 132 determines that the horse takes the left back leg off the ground at midpoints in time between the time when the horse takes the right front leg off the ground and the time when the horse takes the left front leg off the ground. In addition, the first determiner 132 determines that the horse takes the right back leg off the ground at midpoints in time between the time when the horse takes the left front leg off the ground and the time when the horse takes the right front leg off the ground.

The first determiner 132 determines, based on the timing of taking the legs off the ground, the left or right of each of the legs for the timing of putting the front legs on the ground and the timing of putting the back legs on the ground. Specifically, the first determiner 132 determines the timing of putting each of the four legs on the ground. The first determiner 132 outputs information of the determined timing of putting each of the four legs on the ground to the second determiner 133.

In other words, the first determiner 132 determines the timing of putting the legs on the ground based on the top-bottom acceleration included in the received measured data. In addition, the first determiner 132 determines the left or right of each of the legs based on the angular velocity about the yaw axis, determines the front or back of each of the legs based on the acceleration in the top-bottom direction, and determines the timing of putting the left and right back legs based on the timing of putting the left and right front legs on the ground.

Figure 8:
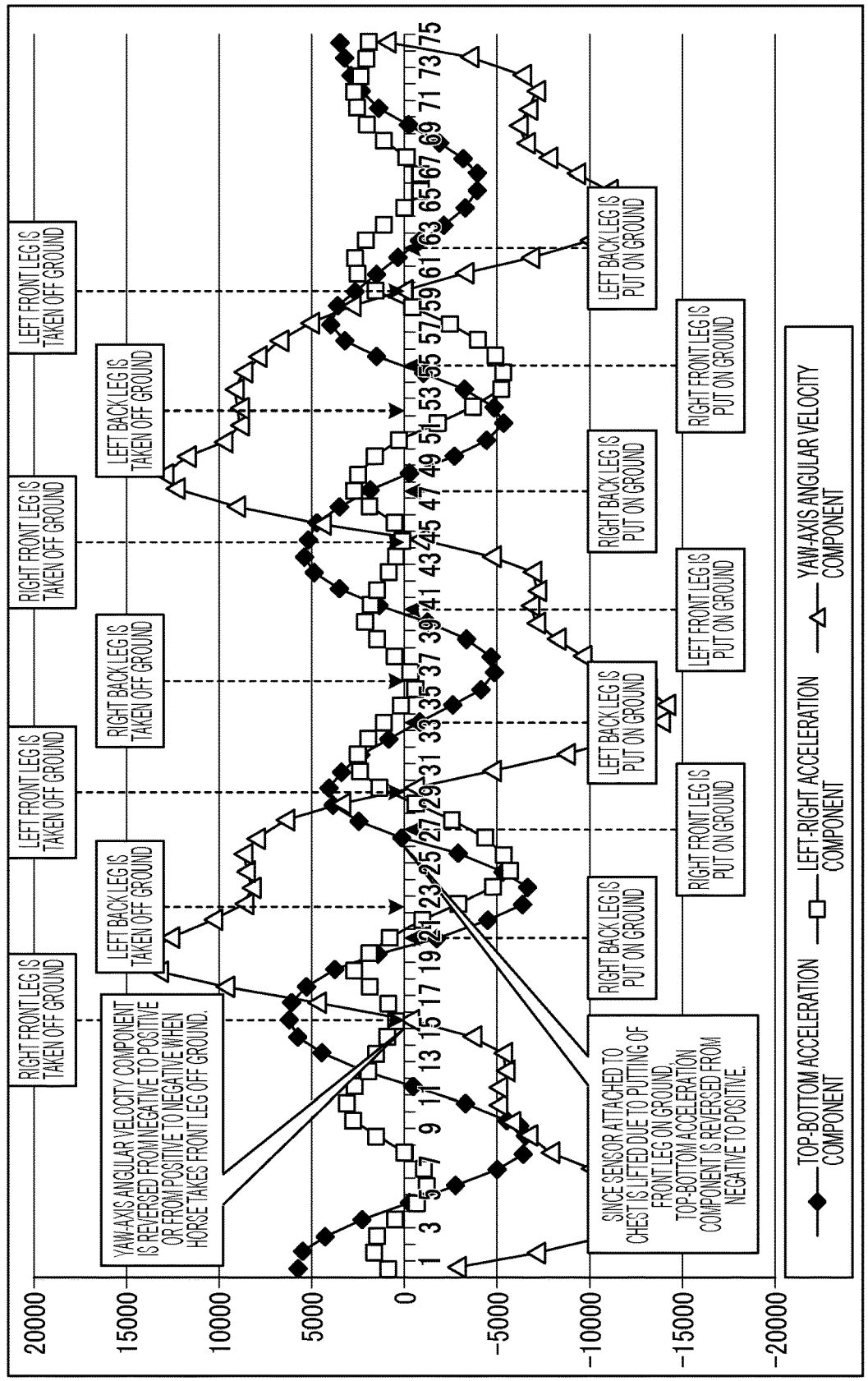
FIG. 8 is a diagram illustrating an example of the timing of taking and putting the legs off and on the ground during walking.

The timing of taking and putting the legs off and on the ground is described with reference to FIGS. 8 and 9. FIG. 8 is a diagram illustrating an example of the timing of taking and putting the legs off and on the ground during walking. A graph 21 illustrated in FIG. 8 indicates the timing of taking and putting legs of a certain horse off and on the ground for data obtained by measuring the certain horse during the time when the certain horse walks. In the example indicating the graph 21, it is determined that the time when the sign of an acceleration component in a top-bottom direction of the horse is reversed from negative to positive is the time when the horse puts a front leg on the ground and that the horse puts one of the back legs on the ground at midpoints in time between the time when the horse puts one of the front legs on the ground and the time when the horse puts the other one of the front legs on the ground and the horse puts the other one of the back legs on the ground at midpoints in time between the time when the horse puts the other one of the front legs on the ground and the time when the horse puts the one of the front legs on the ground. In the example indicating the graph 21, the timing of taking the left and right front legs off the ground is determined based on the time when the sign of an angular velocity component about a yaw axis is reversed from negative to positive and from positive to negative, and it is determined that the horse takes one of the back legs off the ground at midpoints in time between the time when the horse takes one of the front legs off the ground and the time when the horse takes the other one of the front legs off the ground and the horse takes the other one of the back legs off the ground at midpoints in time between the time when the horse takes the other one of the front legs off the ground and the time when the horse takes the one of the front legs off the ground. In the example indicating the graph 21, the left or right of each of the front and back legs put on the ground is determined based on the timing of taking the legs off the ground.

Figure 9:
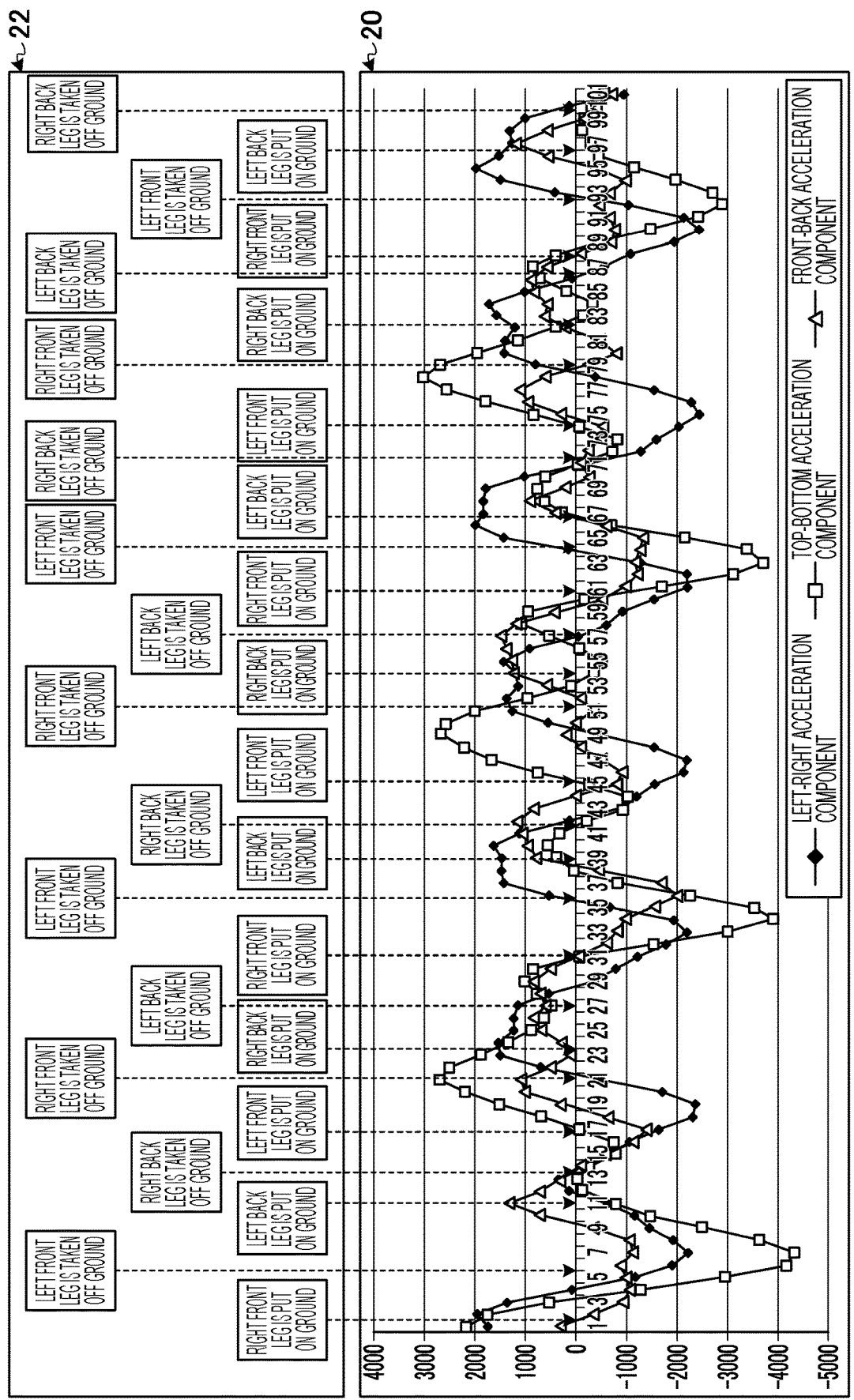
FIG. 9 is a diagram illustrating an example in which the timing of taking and putting the legs off and on the ground is added to the data measured during walking.

FIG. 9 is a diagram illustrating an example in which the timing of taking and putting the legs off and on the ground is added to the data measured during walking. FIG. 9 illustrates the case where timing 22, determined by the first determiner 132, of taking and putting the legs off and on the ground is added to the graph 20 of the measured data illustrated in FIG. 5. In the example illustrated in FIG. 9, the left or right of each of the legs is determined based on the graph using the left-right acceleration component, instead of the yaw-axis angular velocity component. In this case, since the horse body is inclined toward the right side upon the putting of the right back leg on the ground, the left-right acceleration component is positive values before and after the putting of the right back leg on the ground. In addition, since the horse body is inclined toward the left side upon the putting of the left back leg on the ground, the left-right acceleration component is negative values before and after the putting of the left back leg on the ground. The left-right acceleration component may be shifted from the timing of putting the legs on the ground, depending on the horse. Based on the measured data of the graph 20 illustrated in FIG. 9, it is determined that the horse puts the left front leg on the ground when the top-bottom acceleration component is reversed from negative to positive. In addition, although the horse puts the right front leg on the ground when the top-bottom acceleration component is reversed from positive to negative, this is considered to depend on the horse. In this case, for example, it may be determined that the horse puts the right front leg on the ground at midpoints in time between the time when the horse puts the left front leg on the ground and the time when the horse puts the left front leg on the ground next.

Return to FIG. 1. Upon receiving the information of the timing of putting the legs on the ground from the first determiner 132, the second determiner 133 references the measured data storage section 121 and calculates values that are based on the front-back acceleration and correspond to the timing of putting the legs on the ground. For example, the second determiner 133 may use, as the values based on the front-back acceleration, the areas of predetermined ranges of a graph of the front-back acceleration within time intervals between time points when the horse puts legs on the ground or the numbers of plotted values in predetermined ranges of the graph of the front-back acceleration within the time intervals between the time points when the horse puts the legs on the ground. The areas of the predetermined ranges of the graph of the front-back acceleration may include the areas of ranges of the graph during a certain time interval that is included in a time period from the putting of a certain front leg on the ground to the putting of a back leg on the ground immediately after the putting of the certain front leg on the ground and is from the time when the front-back acceleration becomes highest to the time when the front-back acceleration becomes lowest, for example. In addition, the areas of the predetermined ranges of the graph of the front-back acceleration may include the areas of ranges of the graph during a certain time interval that is included in a time period from the putting of a certain back leg on the ground to the putting of a front leg on the ground immediately after the putting of the certain back leg on the ground and is from the time when the front-back acceleration becomes lowest to the time when the front-back acceleration becomes highest, for example.

In addition, for example, the numbers of the plotted values in the predetermined ranges of the graph of the front-back acceleration may include the number of plotted values during a time interval that is included in a time period from the putting of a certain front leg on the ground to the putting of a back leg on the ground immediately after the putting of the certain front leg on the ground and is from the time when the horse puts the certain front leg on the ground to the time when the front-back acceleration becomes highest, and the number of plotted values during a time interval that is included in the time period and is from the time when the front-back acceleration is reversed from positive to negative to the time when the front-back acceleration becomes lowest, for example. Similarly, the numbers of the plotted values in the predetermined ranges of the graph of the front-back acceleration may include the number of plotted values during a time interval that is included in a time period from the putting of a certain back leg on the ground to the putting of a front leg immediately after the putting of the certain back leg on the ground and is from the time when the horse puts the certain back leg on the ground to the time when the front-back acceleration becomes lowest, and the number of plotted values during a time interval that is included in the time period and is from the time when the front-back acceleration is reversed from negative to positive to the time when the front-back acceleration becomes highest.

Figure 10:
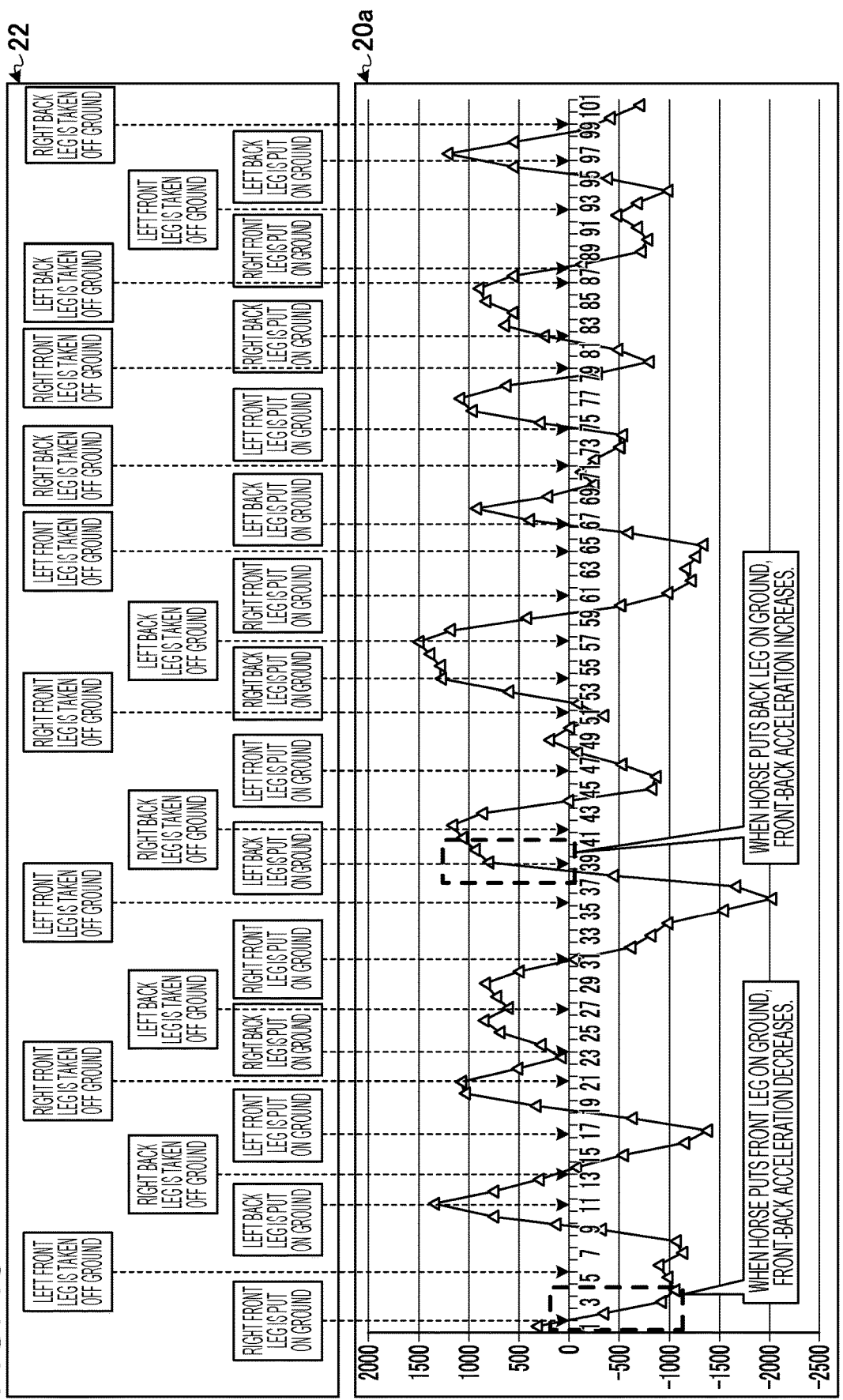
FIG. 10 is a diagram illustrating an example of relationships between the timing of taking and putting the legs off and on the ground and front-back acceleration.

Relationships between the timing of putting the legs on the ground and the front-back acceleration are described with reference to FIGS. 10 and 11. FIG. 10 is a diagram illustrating an example of relationships between the timing of taking and putting the legs off and on the ground during walking and the front-back acceleration. A graph 20a illustrated in FIG. 10 is obtained by extracting a graph of the front-back acceleration from the graph 20 illustrated in FIG. 9. However, the scale of the ordinate (indicating the acceleration) of the graph is enlarged 2 times. The timing 22 of taking and putting the legs off and on the ground is the same as or similar to that illustrated in FIG. 9. It is apparent from the graph 20a that when the horse puts a front leg on the ground, the front-back acceleration decreases or acceleration (hereinafter also referred to as backward acceleration) in a backward direction of the horse occurs. In addition, it is apparent from the graph 20a that when the horse puts a back leg on the ground, the front-back acceleration increases or acceleration (hereinafter referred to as frontward acceleration) in a frontward direction of the horse occurs. If lameness occurs, the inclination of the graph of the front-back acceleration that increases or decreases when the horse puts a leg on the ground becomes larger than that in a normal state or the difference between the highest value of the front-back acceleration and the lowest value of the front-back acceleration becomes larger than that in the normal state. The difference between a graph of the front-back acceleration obtained in the normal state and a graph of the front-back acceleration obtained during lameness varies depending on the horse or physical conditions of the horse.

Figure 11:
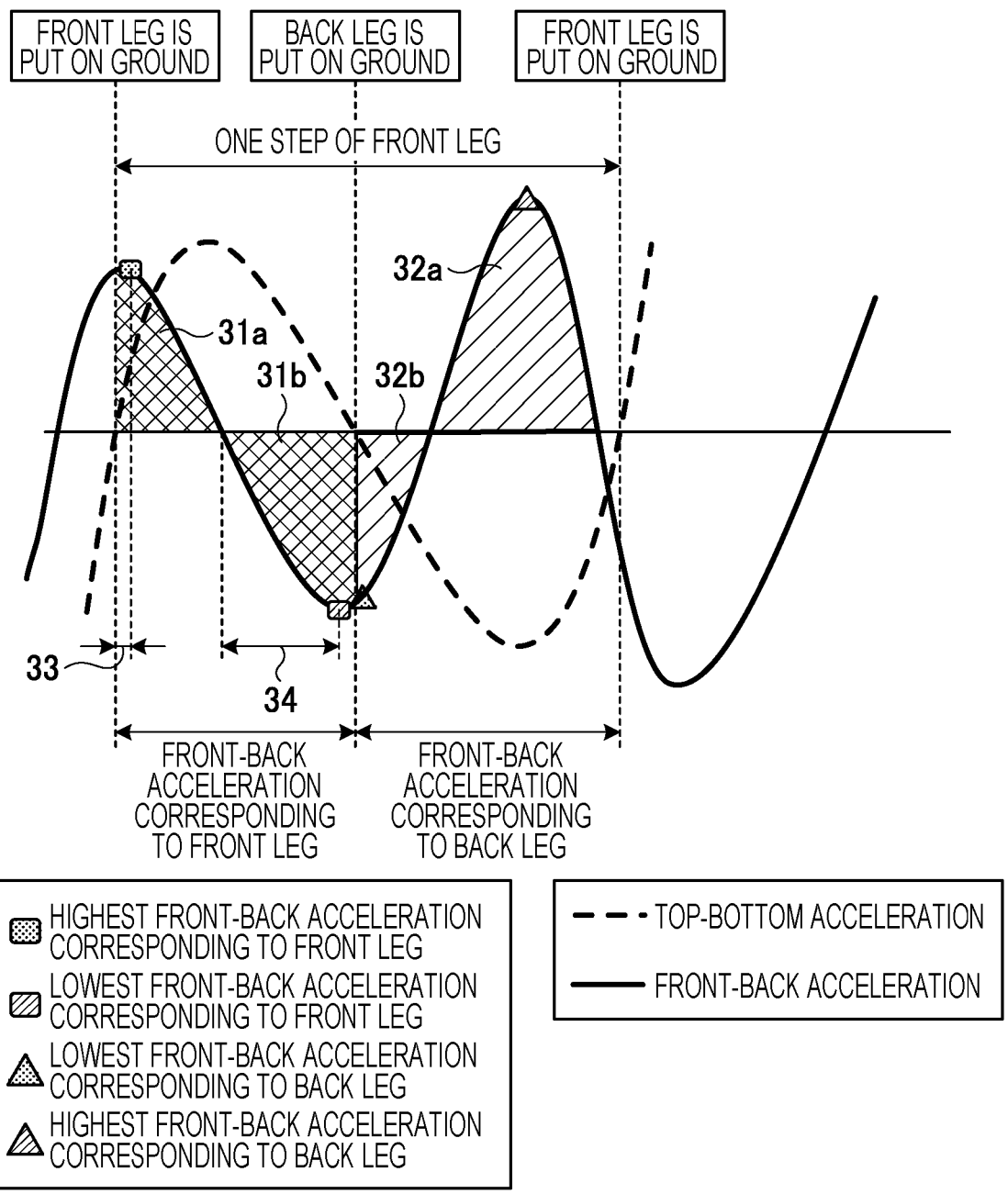
FIG. 11 is a diagram illustrating an example of the front-back acceleration corresponding to the timing of putting the legs on the ground.

FIG. 11 is a diagram illustrating an example of the front-back acceleration corresponding to the timing of putting the legs on the ground. As illustrated in FIG. 11, for example, the area of a predetermined range of a graph of the front-back acceleration corresponding to the timing of putting a front leg on the ground is calculated based on regions 31a and 31b of the graph of the front-back acceleration during a time interval from the time when the horse puts a certain front leg on the ground to the time when the horse puts a back leg on the ground immediately after putting the certain front leg on the ground. In the example illustrated in FIG. 11, the area of the predetermined range of the graph of the front-back acceleration corresponding to the timing of putting the front leg on the ground is calculated by subtracting the area of the region 31b from the area of the region 31a, for example. Specifically, the area is calculated by subtracting the area of the region on the negative side from the area of the region on the positive side in the graph of the front-back acceleration during the time interval between the time when the horse puts the front leg on the ground and the time when the horse puts the back leg on the ground. If the area is expressed by an equation using a time interval of 40 milliseconds during which which data is plotted, the area=Σ (0.04×each plotted value of the front-back acceleration). This equation is used to check how much the horse vibrates in the front-back direction.

Similarly, the area of a predetermined range of the graph of the front-back acceleration corresponding to the timing of putting a back leg on the ground is calculated based on regions 32a and 32b of the graph of the front-back acceleration during a time interval from the time when the horse puts the back leg on the ground to the time when the horse puts a front leg on the ground immediately after putting the back leg on the ground, for example. In the example illustrated in FIG. 11, the area of the predetermined range of the graph of the front-back acceleration corresponding to the timing of putting the back leg on the ground is calculated by subtracting the area of the region 32b from the area of the region 32a, for example. Specifically, in the embodiment, the graph of the front-back acceleration assumes that the acceleration during the time interval from the time when the horse puts the front leg on the ground to the time when the horse puts the back leg on the ground immediately after putting the front leg on the ground is affected by the front leg and that the acceleration during the time interval from the time when the horse puts the back leg on the ground to the time when the horse puts the front leg on the ground immediately after putting the back leg on the ground is affected by the back leg.

As the numbers of plotted values in the predetermined ranges, the number of plotted values in a range 33 that is included in the time interval from the putting of the front leg on the ground to the putting of the back leg on the ground immediately after the putting of the front leg on the ground and is from the time when the horse puts the front leg on the ground to the time when the front-back acceleration becomes highest, and the number of plotted values in a range 34 that is included in the time interval from the putting of the front leg on the ground to the putting of the back leg on the ground immediately after the putting of the front leg on the ground and is from the time when the front-back acceleration is reversed from positive to negative to the time when the front-back acceleration becomes lowest may be used. In the example illustrated in FIG. 11, the number of plotted values in a predetermined range of the graph of the front-back acceleration corresponding to the timing of putting the front leg on the ground is calculated by subtracting the number of plotted values in the range 34 from the number of plotted values in the range 33. If the number of plotted values is used, as the number of plotted values is smaller, the horse has moved more abruptly. If the number of plotted values is a negative value, the number of plotted values may be corrected by adding a correction value to the number of plotted values in the range 33, for example.

Subsequently, the second determiner 133 calculates values that are based on the front-back acceleration and correspond to the timing of putting the legs on the ground, or calculates the areas of predetermined ranges of the graph of the front-back acceleration within time intervals between time points when the horse puts legs on the ground, or calculates the numbers of plotted values of the graph of the front-back acceleration within the time intervals, and classifies the values into groups A, B, and C for each of the legs, for example. Specifically, the second determiner 133 uses the ABC analysis or the like to classify the values into the groups, for example. The number of groups into which the values are classified is not limited to 3 and may be an arbitrary number of 2 or more. In this case, values including the maximum value and close to the maximum value correspond to the group A, and values including the minimum value and close to the minimum value correspond to the group C.

First, the second determiner 133 calculates a threshold for the groups A and B and a threshold for the groups B and C to classify the values into the three groups A, B, and C. In order to calculate the threshold for the groups A and B and the threshold for the groups B and C, the second determiner 133 calculates an average, a variance, and a standard deviation based on the areas of predetermined ranges of the graph of the front-back acceleration within time periods (time intervals) between time points when the horse puts the legs on the ground. The second determiner 133 multiplies the standard deviation by ±3 or increases a range to a range of ±3α and treats the standard deviation multiplied by 3 as the threshold for the groups A and B and treats the standard deviation multiplied by −3 as the threshold for the groups B and C. If the number of plotted values is used, the second determiner 133 calculates the average, the variance, and the standard deviation based on the numbers of plotted values in predetermined ranges of the graph of the front-back acceleration within time periods (time intervals) between time points when the horse puts the legs on the ground. The second determiner 133 uses the calculated threshold for the groups A and B and the calculated threshold for the groups B and C to classify, for all time intervals of the measured data, areas associated with the timing of putting the legs on the ground or the numbers of plotted values associated with the timing of putting the legs on the ground into the groups A, B, and C. A threshold for the groups A and B and a threshold for the groups B and C may be calculated for each horse based on past measured data. The second determiner 133 causes the areas classified into the groups or the numbers, classified into the groups, of plotted values, or the numbers of times that the horse puts each leg on the ground or the ratios of the numbers of times that the horse puts each leg on the ground to be stored as analyzed data in the analyzed data storage section 122.

After classifying the areas associated with the timing of putting the legs on the ground or the numbers of plotted values into the groups, the second determiner 133 extracts a group satisfying a first requirement or groups satisfying a second requirement for each leg based on numbers belonging to the groups A and C. The first requirement is that a number (or a number classified into a group) belonging to a group is equal to or larger than a predetermined value (of, for example, "16 to 18"). The second requirement is that a number (or a number classified into a group) belonging to any of the groups A and C is equal to or smaller than a first value (of, for example, "0 to 2") and that a number (or a number classified into a group) belonging to the other of the groups A and C is equal to or larger than a second value (of, for example, "10"). The first and second requirements may be defined using ratios (percentages). For example, the predetermined value used for the first requirement may be "1.00%", the first value used for the second requirement may be "0.06%", and the second value used for the second requirement may be "0.33%".

Figure 12:
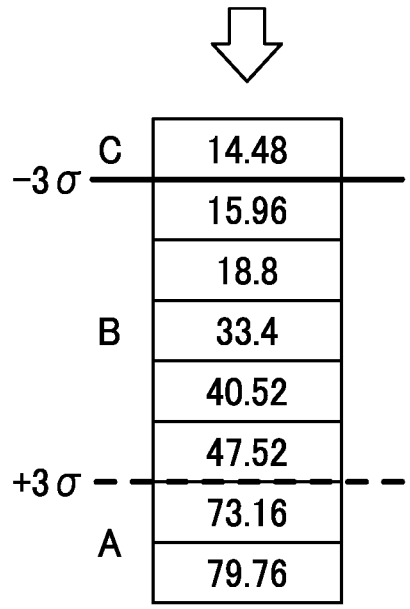
FIG. 12 is a diagram illustrating an example of the classification of areas associated with the timing of putting the legs on the ground.

The classification of the areas associated with the timing of putting the legs on the ground is described with reference to FIG. 12. FIG. 12 is a diagram illustrating an example of the classification of areas associated with the timing of putting the legs on the ground. The second determiner 133 uses the threshold (+3α) for the groups A and B and the threshold (−3α) for the groups B and C to classify each of the areas associated with the timing of putting the legs on the ground into any of the three groups A, B, and C. The example illustrated in FIG. 12 assumes that the threshold for the groups A and B is "50" and that the threshold for the groups B and C is "15". If a certain area is larger than "50", the second determiner 133 classifies the certain area into the group A. If the certain area is smaller than "15", the second determiner 133 classifies the certain area into the group C. In addition, if the certain area is equal to or larger than "15" and equal to or smaller than "60", the second determiner 133 classifies the certain area into the group B.

When the classification of the areas into the groups is completed for all the time intervals of the measured data, the second determiner 133 calculates, for each of the legs, the number, belonging to each group, of times that the horse has put the leg on the ground. In a table 35, in a row indicating the right front leg, the group A for the right legs indicates "0", the group B for the right legs indicates "3056", the group C for the right legs indicates "18", and the groups A, B, and C for the left legs indicate "0". In a row indicating the left front leg, the group A for the left legs indicates "9", the group B for the left legs indicates "3310", the group C for the left legs indicates "15", and the groups A, B, and C for the right legs indicate "0". In a row indicating the left back leg, the group A for the left legs indicates "1", the group B for the left legs indicates "3105", the group C for the left legs indicates "41", and the groups A, B, and C for the right legs indicate "0". In a row indicating the right back leg, the group A for the right legs indicates "16", the group B for the right legs indicates "3082", the group C for the right legs indicates "0", and the groups A, B, and C for the left legs indicate "0". The second determiner 133 causes the results of the classification to be stored as analyzed data in the analyzed data storage section 122.

In the example indicating the table 35, the second determiner 133 extracts, as a group satisfying the first requirement, a group 36 that is indicated in the row indicating the left back leg and is indicated in a column indicating the group C for the left legs. In addition, in the example indicating the table 35, the second determiner 133 extracts, as groups satisfying the second requirement, groups 37a and 37c indicated in the row indicating the right front leg, groups 38a and 38c indicated in the row indicating the left back leg, and groups 39a and 39c indicated in the row indicating the right back leg.

Next, the second determiner 133 determines whether or not the second determiner 133 has extracted a group satisfying the first requirement or groups satisfying the second requirement. If the second determiner 133 determines that the second determiner 133 has not extracted the group satisfying the first requirement or the groups satisfying the second requirement, the second determiner 133 determines that a lame leg has not been detected, and the second determiner 133 causes the display section 111 to display a determination result indicating that a lame leg has not been detected.

If the second determiner 133 determines that the second determiner 133 has extracted the group satisfying the first requirement or the groups satisfying the second requirement, the second determiner 133 determines a lame leg based on a lame leg determination table and the extracted group or groups for each leg. The second determiner 133 causes the display section 111 to display the result of determining the lame leg.

The lame leg determination table is described below with reference to FIG. 13. FIG. 13 is a diagram illustrating an example of the lame leg determination table. A lame leg determination table 40 illustrated in FIG. 13 includes a table 41 and a table 42. The table 41 indicates whether or not legs other than a lame leg are affected by the lameness upon the putting of the lame leg on the ground. In the table 41, each lame leg is associated with information indicating whether or not legs other than the lame leg are affected by the lameness upon the putting of the lame leg on the ground. The table 42 indicates changes in behaviors of each lame leg and the other legs. The lame leg determination table 40 is an example of a determination table indicating relationships between lame legs and increasing or decreasing trends in acceleration in the front-back direction. For example, a first column of the lame leg determination table 40 indicates that if the right front leg is lame, the right back leg is not affected by the lameness upon the putting of the lame right front leg on the ground, and the left front leg and the left back leg are affected by the lameness upon the putting of the lame right front leg on the ground. In addition, the first column of the lame leg determination table 40 indicates that backward acceleration that normally occurs is reduced upon the putting of the lame right front leg on the ground. When the horse puts the right back leg on the ground, normal forward acceleration occurs. When the horse puts the left front leg on the ground, the left front leg is slightly affected by the lameness, and normal backward acceleration occurs. Since the horse puts the left back leg on the ground after putting the lame leg (right front leg) on the ground, and quickly puts the left back leg on the ground to protect the painful right front leg, forward acceleration that normally occurs is reduced. Similarly, second to fourth columns of the lame leg determination table 40 indicate relationships between each lame leg and the other legs whose behaviors change upon the putting of the lame leg on the ground.

For example, the extracted groups 36, 37a, 37c, 38a, 38c, 39a, and 39c illustrated in FIG. 12 are applied to the lame leg determination table 40 illustrated in FIG. 13. Since the group 36 satisfying the first requirement belongs to the group C and indicates the putting of the left back leg on the ground, areas associated with the timing of putting the left back leg on the ground are small or the front-back acceleration is reduced compared with the normal state, the second determiner 133 determines that the right front leg or the left back leg is lame. The groups 37a and 37c satisfying the second requirement belong to the groups A and C, respectively and indicate the putting of the right front leg on the ground. The groups 37a and 37c indicate that there is no case where an area associated with the timing of putting the right front leg on the ground is larger than the threshold for the groups A and B and the number of times that an area associated with the timing of putting the right front leg on the ground is smaller than the threshold for the groups B and C is in the normal range. Thus, the second determiner 133 determines, based on the groups 37a and 37c, that the right front leg is lame.

The groups 38a and 38c belong to the groups A and C, respectively and indicate the putting of the left back leg on the ground. The groups 38a and 38c indicate that the number of times that an area associated with the timing of putting the left back leg on the ground is larger than the threshold for the groups A and B is small, and that the number of times that an area associated with the timing of putting the left back leg on the ground is smaller than the threshold for the groups B and C is large. Thus, the second determiner 133 determines, based on the groups 38a and 38c, that the right front leg or the left back leg is lame. The group 38c is the same group as the group 36. However, since whether or not a combination of the groups 38a and 38c satisfies the second requirement is determined, the different reference symbols are used.

The groups 39a and 39c belong to the groups A and C, respectively and indicate the putting of the right back leg on the ground. The groups 39a and 39c indicate that the number of times that an area associated with the timing of putting the right back leg on the ground is larger than the threshold for the groups A and B is in the normal range and there is no case where an area associated with the timing of putting the right back leg on the ground is smaller than the threshold for the groups B and C. Thus, since there is no case where the forward acceleration is reduced, the second determiner 133 determines, based on the groups 39a and 39c, that the right back leg and the left front leg are not lame. The second determiner 133 determines that the right front leg is lame, since the number of times that the right front leg is determined to be lame is the largest among the results of making the determination based on the groups 36, 37a, 37c, 38a, 38c, 39a, and 39c.

As indicated in a cell that is included in the second column of the lame leg determination table 40 illustrated in FIG. 13 and is included in a row indicating the putting of the right front leg on the ground and a cell that is included in the fourth column of the lame leg determination table 40 illustrated in FIG. 13 and is included in a row indicating the putting of the left front leg on the ground, forward acceleration occurs without the occurrence of backward acceleration that normally occurs. If this requirement is satisfied, the second determiner 133 may determine that the right back leg is lame based on the occurrence of the forward acceleration upon the putting of the right front leg on the ground, and the second determiner 133 may determine that the left back leg is lame based on the occurrence of the forward acceleration upon the putting of the left front leg on the ground. In addition, if one or multiple requirements indicated in cells included in the first column of the lame leg determination table 40 and included in the row indicating the putting of the right front leg on the ground and a row indicating the putting of the left back leg on the ground are satisfied, the second determiner 133 may determine that the right front leg is lame. Furthermore, if one or multiple requirements indicated in cells included in the third column of the lame leg determination table 40 and included in a row indicating the putting of the right back leg on the ground and the row indicating the putting of the left front leg on the ground are satisfied, the second determiner 133 may determine that the left front leg is lame.

In other words, the second determiner 133 determines whether or not the legs are injured based on values, corresponding to the determined timing of putting the legs on the ground, of the acceleration in the front-back direction. In addition, the second determiner 133 determines whether or not each of the legs is injured based on values, corresponding to the determined timing of putting each of the legs on the ground, of the acceleration in the front-back direction. Furthermore, the second determiner 133 classifies, into the multiple groups for each of the legs, the areas of ranges of a graph of the front-back acceleration within time intervals between multiple time points when the horse puts the target leg on the ground and when the horse puts another leg on the ground immediately after putting the target leg on the ground, and the second determiner 133 determines whether or not each of the legs is injured based on the numbers, classified into the group of values including the maximum value and close to the maximum value and the group of values including the minimum value and close to the minimum value, of times that the horse puts the legs on the ground. Furthermore, the second determiner 133 classifies, into the multiple groups for each of the legs, the numbers of plotted values of the graph of the acceleration in the front-back direction within time intervals between multiple time points when the horse puts the target leg on the ground and when the horse puts another leg on the ground immediately after putting the target leg on the ground, and the second determiner 133 determines whether or not each of the legs is injured based on the numbers, classified into the group of values including the maximum value and the group of values including the minimum value, of times that the horse puts the legs on the ground. Furthermore, the second determiner 133 uses the determination table indicating relationships between lame legs and increasing or decreasing trends in acceleration in the front-back direction to determine a lame leg based on the increasing or decreasing trends, indicated by the numbers of times that the horse puts the legs on the ground, in the acceleration in the front-back direction.

Figure 14:
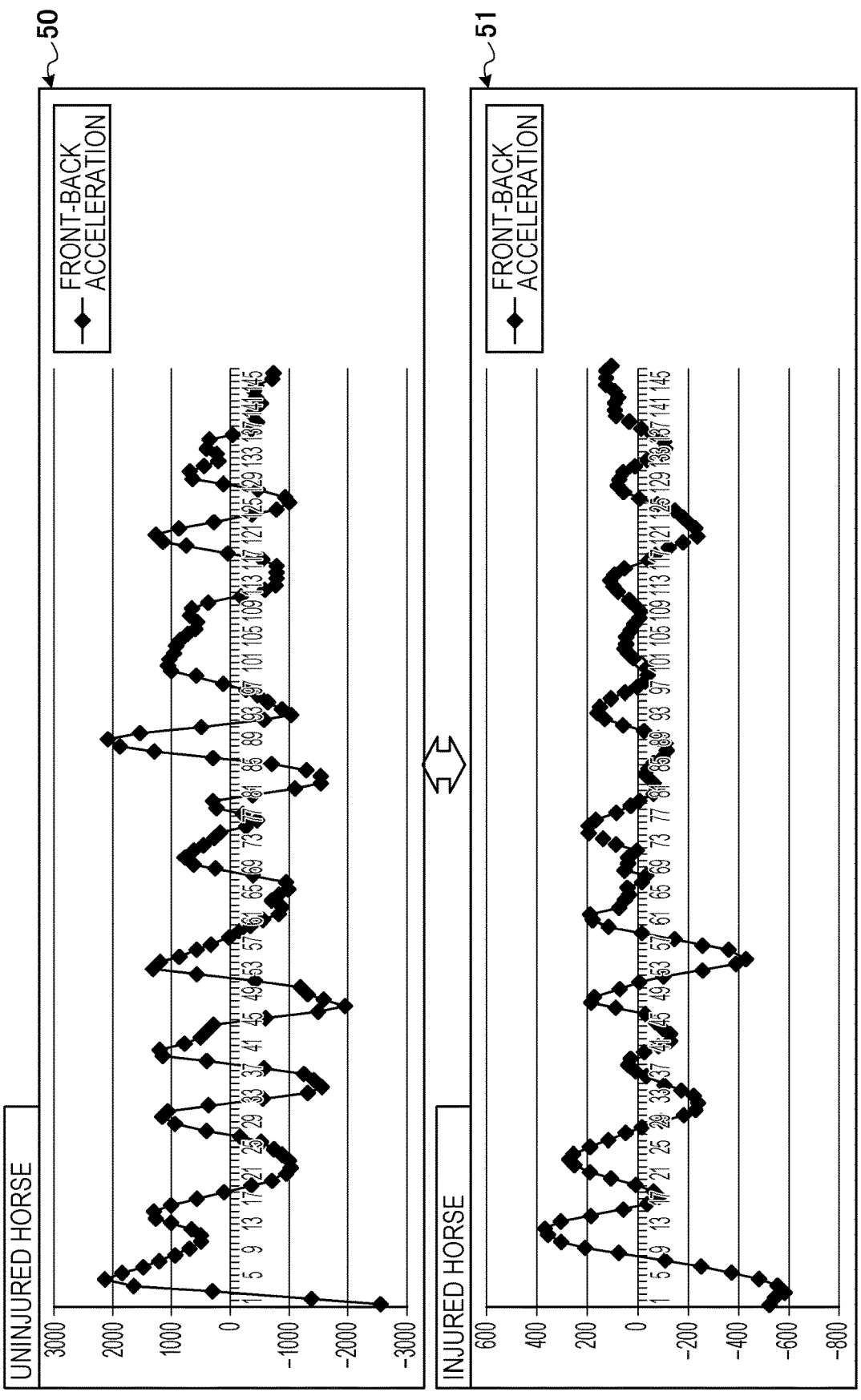
FIG. 14 is a diagram illustrating an example of the comparison of waveforms of the front-back acceleration.

The comparison of waveforms of the front-back acceleration is described with reference to FIG. 14. FIG. 14 is a diagram illustrating an example of the comparison of the waveforms of the front-back acceleration. In the example illustrated in FIG. 14, a graph 50 that indicates an uninjured horse indicates a waveform of the front-back acceleration that repeatedly changes in a regular manner, and a graph 51 that indicates an injured horse indicates a waveform of the front-back acceleration that changes in an irregular manner. If the horse is injured, the waveform of the front-back acceleration is disturbed as described above. In the example illustrated in FIG. 14, since the horse indicated by the graph 50 and the horse indicated by the graph 51 are different, the difference between a range of values of the front-back acceleration of the horse indicated by the graph 50 and a range of values of the front-back acceleration of the horse indicated by the graph 51 is caused by the difference between the horses.

Figure 15:
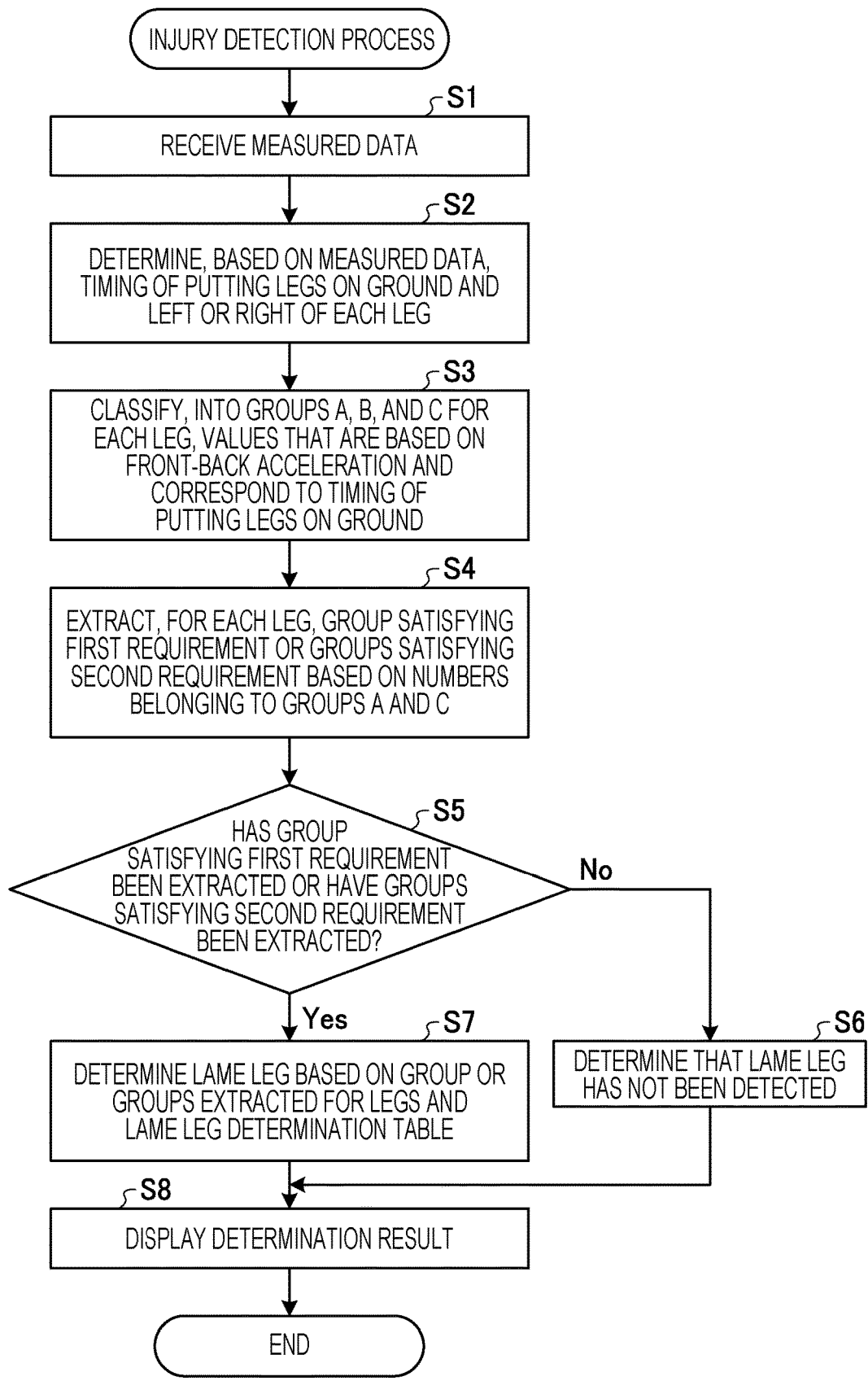
FIG. 15 is a flowchart illustrating an example of an injury detection process according to the embodiment.

Next, operations of the injury detecting device 100 according to the embodiment are described. FIG. 15 is a flowchart illustrating an example of an injury detection process according to the embodiment.

The receiver 131 receives the measured data from the chest sensor 10 (in step S1). The receiver 131 causes the received measured data to be stored in the measured data storage section 121. After the measured data is stored in the measured data storage section 121, the receiver 131 outputs, to the first determiner 131, an instruction to determine the timing of putting the legs on the ground.

Upon receiving the instruction to determine the timing of putting the legs on the ground from the receiver 131, the first determiner 131 references the measured data storage section 121 and determines, based on the measured data, the timing of putting each of the legs on the ground and the left or right of each of the legs (in step S2). The first determiner 132 outputs information of the timing of putting each of the legs on the ground to the second determiner 133.

Upon receiving the information of the timing of putting each of the legs on the ground from the first determiner 132, the second determiner 133 references the measured data storage section 121 and calculates values that are based on the front-back acceleration and correspond to the timing of putting the legs on the ground. The second determiner 133 classifies, into the groups A, B, and C for each of the legs, the values that are based on the front-back acceleration and correspond to the timing of putting the legs on the ground (in step S3).

After classifying, into the groups, the values that are based on the front-back acceleration and correspond to the timing of putting the legs on the ground, the second determiner 133 extracts, for each of the legs, a group satisfying the first requirement or groups satisfying the second requirement based on numbers belonging to the groups A and C (in step S4). The second determiner 133 determines whether or not the second determiner 133 has extracted the group satisfying the first requirement or the groups satisfying the second requirement (in step S5).

If the second determiner 133 determines that the second determiner 133 has not extracted the group satisfying the first requirement or the groups satisfying the second requirement (No in step S5), the second determiner 133 determines that a lame leg has not been detected (in step S6). The second determiner 133 causes the display section 111 to display a determination result indicating that a lame leg has not been detected (in step S8).

On the other hand, if the second determiner 133 determines that the second determiner 133 has extracted the group satisfying the first requirement or the groups satisfying the second requirement (Yes in step S5), the second determiner 133 determines a lame leg based on the group or groups extracted for each leg and the lame leg determination table (in step S7). The second determiner 133 causes the display section 111 to display the result of determining the lame leg (in step S8). Thus, the injury detecting device 100 may detect an injury without causing physical stress.

In the aforementioned embodiment, the top-bottom acceleration, the left-right acceleration, the front-back acceleration, and the yaw-axis angular velocity, which are based on the gait of the horse, are used to determine whether or not each of the legs is lame and detect whether or not each of the legs of the horse is injured. The embodiment, however, is not limited to this. For example, the top-bottom acceleration and the top-bottom acceleration may be used to detect whether or not a front or back leg of the horse is injured.

In the aforementioned embodiment, whether or not each of the legs of the horse is injured is detected based on the data measured during the time when the horse walks. The embodiment, however, is not limited to this. For example, as long as another quadruped puts its legs on the ground in the same order as the walk of a horse, the injury detection system may detect whether or not each of the legs of the other quadruped is injured.

As described above, the injury detecting device 100 receives measured data that is based on the gait of the quadruped and includes acceleration in a top-bottom direction of the quadruped and acceleration in a front-back direction of the quadruped. In addition, the injury detecting device 100 determines the timing of putting the legs of the quadruped on the ground based on the acceleration, included in the received measured data, in the top-bottom direction. In addition, the injury detecting device 100 determines whether or not each of the legs is injured based on values, corresponding to the determined timing of putting the legs on the ground, of the acceleration in the top-back direction. As a result, the injury detecting device 100 may detect an injury without causing physical stress.

In addition, the injury detecting device 100 receives the data measured during the time when the gait of the quadruped is walk. As a result, the injury detecting device 100 may detect an injury from the data measured during walking without causing physical stress.

In addition, the measured data received by the injury detecting device 100 further includes an angular velocity about a yaw axis. The injury detecting device 100 determines the left or right of each of the legs based on the angular velocity about the yaw axis, determines the front or back of each of the legs based on the acceleration in the top-bottom direction, and determines the timing of putting the left and right back legs on the ground based on the timing of putting the left and right front legs on the ground. In addition, the injury detecting device 100 determines whether or not each of the legs is injured based on values, corresponding to the determined timing of putting each of the legs on the ground, of the acceleration in the front-back direction. As a result, the injury detecting device 100 may determine whether or not any of the four legs is injured.

In addition, the injury detecting device 100 classifies, into multiple groups for each of the legs, the areas of ranges of a graph of the acceleration in the front-back direction within time intervals between multiple time points when the quadruped puts the target leg on the ground and when the quadruped puts another leg on the ground immediately after putting the target leg on the ground, and the injury detecting device 100 determines whether or not each of the legs is injured based on the numbers, classified into a group of values including the maximum value and close to the maximum value and a group of values including the minimum value and close to the minimum value, of times that the quadruped puts the legs on the ground. As a result, the injury detecting device 100 may determine whether or not any of the legs is injured.

In addition, the injury detecting device 100 classifies, into the multiple groups for each of the legs, the numbers of plotted values of the graph of the acceleration in the front-back direction within time intervals between multiple time points between the quadruped puts the legs on the ground. Furthermore, the injury detecting device 100 determines whether or not each of the legs is injured based on the numbers, classified into the group of values including the maximum value and close to the maximum value and the group of values including the minimum value and close to the minimum value, of times that the quadruped puts the legs on the ground. As a result, the injury detecting device 100 may determine whether or not any of the four legs is injured.

In addition, the injury detecting device 100 uses a determination table indicating relationships between lame legs and increasing or decreasing trends in the acceleration in the front-back direction to determine a lame leg based on the increasing or decreasing trends, indicated by the numbers of times that the quadruped puts the legs on the ground, of the acceleration in the front-back direction. As a result, the injury detecting device 100 may determine whether or not any of the four legs is injured.

The constituent elements of the sections illustrated in the drawings may not be physically configured as illustrated in the drawings. Specifically, the specific forms of the distribution and integration of the sections are not limited to those illustrated in the drawings, and all or a portion of the sections may be functionally or physically distributed and integrated in arbitrary units, depending on various loads, usage states, and the like. For example, the receiver 131 and the first determiner 133 may be integrated with each other. In addition, the processes illustrated may not be executed in the aforementioned order. Two or more of the processes may be executed at the same time without the contradiction of the details of the processes, or the processes may be executed in different order without the contradiction of the details of the processes.

In addition, all or an arbitrary portion of the various processing functions that are executed in the devices may be executed by a CPU (or a microcomputer such as an MPU or a micro controller unit (MCU)). In addition, it goes without saying that all or a portion of the various processing functions may be executed by a program analyzed and executed by the CPU (or the microcomputer such as the MPU or the MCU) or by hardware with wired logic.

Figure 16:
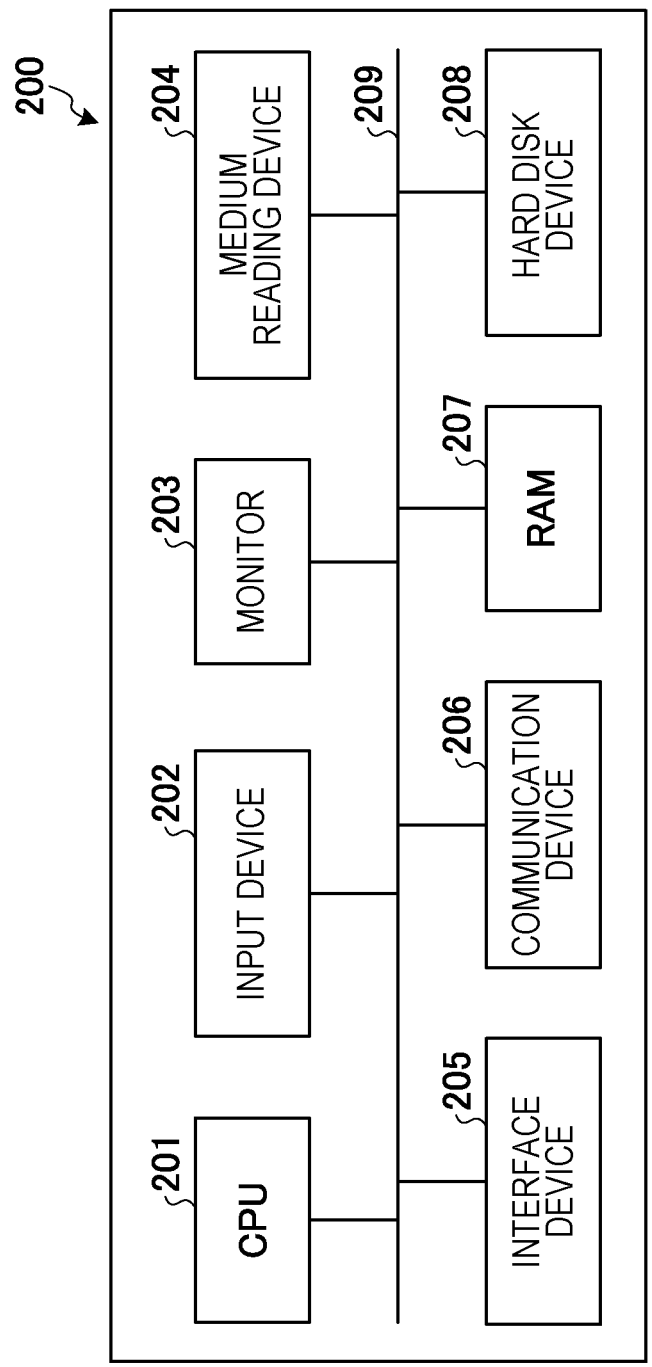
FIG. 16 is a diagram illustrating an example of a computer that executes a program for detecting an injury of a quadruped.

The various processes that are described in the aforementioned embodiment may be achieved by causing a computer to execute a program prepared in advance. An example of the computer that executes the program having the same functions as those described in the embodiment is described below. FIG. 16 is a diagram illustrating an example of the computer that executes the program for detecting an injury of a quadruped.

As illustrated in FIG. 16, a computer 200 includes a CPU 201 that executes various types of arithmetic processing, an input device 202 that receives input data, and a monitor 203. The computer 200 also includes a medium reading device 204 that reads the program and the like from a storage medium, an interface device 205 that is connected to various devices, and a communication device 206 that is connected to another information processing device or the like wirelessly or via a cable. The computer 200 also includes a RAM 207 that temporarily stores various types of information, and a hard disk device 208. The devices 201 to 208 are connected to a bus 209.

In the hard disk device 208, the program for detecting an injury of a quadruped is stored. The program for detecting an injury of a quadruped has the same functions as the processing sections that are the receiver 131, the first determiner 132, and the second determiner 133, which are illustrated in FIG. 1. In addition, in the hard disk device 208, various types of data that achieve the measured data storage section 121, the analyzed data storage section 122, and the program for detecting an injury of a quadruped are stored. The input device 202 receives various types of input information such as operational information from a user of the computer 200, for example. The monitor 203 displays various screens including an output screen to the user of the computer 200, for example. The medium reading device 204 reads the measured data from the storage medium. The interface device 205 is connected to a printing device or the like, for example. The communication device 206 is connected to the chest sensor 10 and communicates various types of information such as the measured data with the chest sensor 10.

The CPU 201 reads the program, stored in the hard disk device 208, for detecting an injury of a quadruped, loads the read program into the RAM 207, and executes the program, thereby executing the various processes. In addition, the program may cause the computer 200 to function as the receiver 131, the first determiner 132, and the second determiner 133, which are illustrated in FIG. 1.

The aforementioned program for detecting an injury of a quadruped may not be stored in the hard disk device 208. For example, the computer 200 may read the program stored in a storage medium readable by the computer 200 and execute the read program. The storage medium readable by the computer 200 corresponds to a CD-ROM, a DVD, a portable recording medium such as a USB memory, a semiconductor memory such as a flash memory, a hard disk drive, or the like, for example. In addition, the program for detecting an injury of a quadruped may be stored in a device connected to a public line, the Internet, a LAN, or the like, and the computer 200 may read the program for detecting an injury of a quadruped from the public line, the Internet, the LAN, or the like and execute the read program for detecting an injury of a quadruped.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiments of the present invention have been described in detail, it should be understood that the various changes, substitutions, and alterations could be made hereto without departing from the spirit and scope of the invention.

What is claimed is:

1. A device for detecting an injury of a quadruped, comprising:
    a memory;
    and a processor coupled to the memory and configured to execute a process including:
    receiving measured data measured by an acceleration sensor attached to a front chest region of a quadruped, the measured data being based on a gait of walk of the quadruped and includes acceleration in a top-bottom direction and acceleration in a front-back direction, the measured data indicating a movement of the chest region of the quadruped;
    first determining timings of putting legs of the quadruped on a ground based on the acceleration in the top-bottom direction, included in the received measured data;
    and second determining whether or not each of the legs is Injured based on values, corresponding to the determined timings of putting the legs on the ground, of the acceleration in the front-back direction;
    classifying the measured data into multiple groups for each of the legs based on the timings of putting legs of the quadruped on the ground and the acceleration in the front-back direction within time intervals between multiple time points when the quadruped puts a target leg on the ground and when the quadruped puts another leg on the ground immediately after the target leg on the ground;
    and detecting an injury to the quadruped based on the values within more than one of the classified groups.

2. The device according to claim 1, wherein the measured data further includes an angular velocity about a yaw axis, wherein the first determining includes determining a left or a right of each of the legs based on the angular velocity about the yaw axis, determining front or back of each of the legs based on the acceleration in the top-bottom direction, and determining timings of putting the left and right back legs on the ground based on the timings of putting the left and right front legs on the ground, and wherein the second determining includes determining whether or not each of the legs is injured based on the values, corresponding to the determined timings of putting the legs on the ground, of the acceleration in the front-back direction.

3. The device according to claim 2, wherein the classifying classifies, into the multiple groups for each of the legs, areas of ranges of a graph of the acceleration in the front-back direction within time intervals between multiple time points when the quadruped puts the target leg on the ground and when the quadruped puts another leg on the ground immediately after the target leg on the ground;

and the detecting the injury detects whether or not each of the legs is injured based on a number, classified into a group of values including a maximum value and another group of values including a minimum value, of times that the quadruped puts the legs on the ground.

4. The device according to claim 3, wherein in the second determining, a lame leg is determined based on an increasing or decreasing trend in the acceleration in the front-back direction by referring to a determination table indicating relationships between lame legs and increasing or decreasing trends in the acceleration in the front-back direction represented by the numbers of times that the quadruped puts the legs on the ground.

5. The device according to claim 2, wherein the classifying classifies, into the multiple groups for each of the legs, the numbers of plotted values of a graph of the acceleration in the front-back direction within time intervals between multiple time points when the quadruped puts the target leg on the ground and when the quadruped puts another leg on the ground immediately after putting the target leg on the ground; and the detecting the injury detects whether or not each of the legs is injured based on a number, classified into a group of values including a maximum value and another group of values including a minimum value, of times that the quadruped puts the legs on the ground.

6. A method for detecting an injury of a quadruped, performed by a computer, the method comprising:

receiving measured data measured by an acceleration sensor attached to a front chest region of a Quadruped, the measured data being based on a gait of walk of the quadruped and includes acceleration in a top-bottom direction and acceleration in a front-back direction, the measured data indicating a movement of the chest region of the quadruped;

first determining timings of putting legs of the quadruped on a ground based on the acceleration in the top-bottom direction, included in the received measured data;

and second determining whether or not each of the legs is injured based on values, corresponding to the determined timings of putting the legs on the ground, of the acceleration in the front-back direction;

classifying the measured data into multiple groups for each of the legs based on the timings of putting legs of the quadruped on the ground and the acceleration in the front-back direction within time intervals between multiple time points when the quadruped puts a target leg on the ground and when the quadruped puts another leg on the ground immediately after the target leg on the ground;

and detecting an injury to the quadruped based on the values within more than one of the classified groups.

7. A non-transitory computer-readable storage medium storing a program for detecting an injury of a quadruped, the program causes a computer, when executed, to perform a process comprising:

first determining timings of putting legs of a quadruped on a ground based on acceleration in the top-bottom direction, included in received measured data measured by an acceleration sensor attached to a front chest region of the quadruped, the measured data indicating a movement of the chest region of the quadruped;

and second determining whether or not each of the legs is injured based on values, corresponding to the determined timings of putting the legs on the ground, of acceleration in the front-back direction included in the received measured data;

classifying the measured data into multiple groups for each of the legs based on the timings of putting legs of the quadruped on the ground and the acceleration in the front-back direction within time intervals between multiple time points when the quadruped puts a target leg on the ground and when the quadruped puts another leg on the ground immediately after the target leg on the ground;

and detecting an injury to the quadruped based on the values within more than one of the classified groups.

* * * * *